US008633450B2

(12) United States Patent
Cunningham

(10) Patent No.: US 8,633,450 B2
(45) Date of Patent: Jan. 21, 2014

(54) APPARATUS FOR ASSISTING DETERMINATION OF DETECTIVE QUANTUM EFFICIENCY

(75) Inventor: Ian Cunningham, London (CA)

(73) Assignee: DQE Instruments Inc., London (CA)

( * ) Notice: Subject to any disclaimer, the term of this patent is extended or adjusted under 35 U.S.C. 154(b) by 642 days.

(21) Appl. No.: 12/527,669

(22) PCT Filed: Feb. 19, 2008

(86) PCT No.: PCT/CA2008/000304
§ 371 (c)(1),
(2), (4) Date: Aug. 18, 2009

(87) PCT Pub. No.: WO2008/101322
PCT Pub. Date: Aug. 28, 2008

(65) Prior Publication Data
US 2010/0012842 A1     Jan. 21, 2010

Related U.S. Application Data

(60) Provisional application No. 60/890,518, filed on Feb. 19, 2007.

(51) Int. Cl.
*G01T 1/161* (2006.01)
(52) U.S. Cl.
USPC .......................................... 250/393; 378/207
(58) Field of Classification Search
USPC .......................................... 250/393; 378/207
See application file for complete search history.

(56) References Cited

U.S. PATENT DOCUMENTS

| 3,654,468 | A | * | 4/1972 | Shah | 250/302 |
| 4,077,721 | A | * | 3/1978 | Mohon | 356/124 |
| 5,115,134 | A | * | 5/1992 | Slowey | 250/374 |
| 5,442,674 | A | * | 8/1995 | Picard et al. | 378/20 |
| 6,521,886 | B2 | | 2/2003 | Aufrichtig et al. | |
| 6,784,433 | B2 | | 8/2004 | Zur | |
| 7,015,460 | B2 | | 3/2006 | Nelson et al. | |

OTHER PUBLICATIONS

Hadar et al. Numerical calculation of MTF for image motion: experimental verification, Proceedings of SPIE vol. 1697 (Apr. 1992), pp. 183-197.*

(Continued)

*Primary Examiner* — David Porta
*Assistant Examiner* — Shun Lee
(74) *Attorney, Agent, or Firm* — F. Chau & Associates, LLC

(57) ABSTRACT

An apparatus for determining MTF and DQE of an ionizing radiation imaging system/detector is provided, comprising a box having aligned windows transparent to an ionizing radiation beam. When the box is placed in front of the detector, the beam passes through the box. The apparatus further comprises: a KERMA module for measuring incident free-air KERMA; a backscatter baffle for preventing backscatter of the beam from the detector into the KERMA module; a scatter baffle for preventing scatter of the beam into the KERMA module, and to reduce backscatter from the backscatter baffle; at least one MTF module for enabling acquisition of at least one edge image. Each module and the at least one backscatter baffle are independently moveable in and out of the beam, such that open, dark and edge images may be independently acquired, and KERMA module measurements may be performed independent of image acquisition, to determine DQE.

20 Claims, 16 Drawing Sheets

(56) References Cited

OTHER PUBLICATIONS

Illers et al. Measurement of the Detective Quantum Efficiency (DQE) of digital X-ray imaging devices according to the standard IEC 62220-1, Proceedings of SPIE vol. 5368 (Feb. 2004), pp. 177-187.*

Starck et al. The use of detective quantum efficiency (DQE) in evaluating the performance of gamma camera systems, Physics in Medicine and Biology, vol. 50, No. 7 (Mar. 2005), pp. 1601-1609.*

Beutel, J., Kundel, H.L., Van Metter, R.L., "Handbook of Medical Imaging: vol. 1, Physics and Psychophysics"; Chapter 2. Applied Linear-Systems Theory, pp. 1-79, published by SPIE Press, Bellingham, Washington USA, 2000.

Giger, M.L., Doi, K., "Investigation of basic imaging properties in digital radiography", Med. Phys. 11(3), May/Jun. 1984, pp. 287-295.

Samei, E., Flynn, J.J., Reimann, D.A., "A method for me assuring the presampled MTF of digital radiographic systems using an edge test device", Med. Phys. 25(1), Jan. 1998, pp. 102-113.

\* cited by examiner

Images: 20080121-181213
| 1: Calib 1 of 1 | 2: Open 1 of 24 | 3: Open 2 of 24 | 4: Open 3 of 24 |
|---|---|---|---|
| 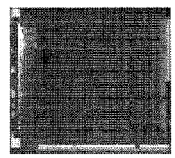 | 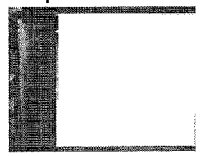 | 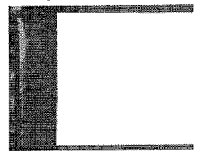 | 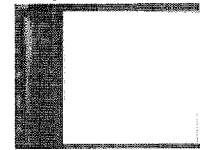 |
| 5: Open 4 of 2 | 6: Open 5 of 24 | 7: Open 6 of 24 | 8: Open 7 of 24 |
| 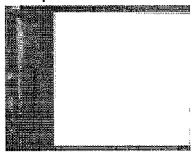 | 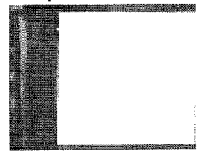 | 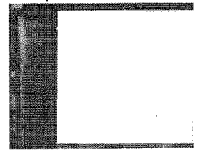 | 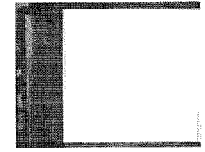 |
| 9: Open 8 of 24 | 10: Open 9 of 24 | 1: Open 10 of 24 | 2: Open 11 of 24 |
| 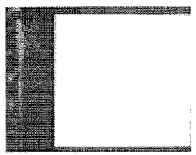 | 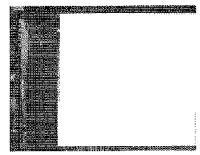 | 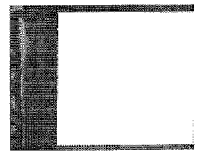 | 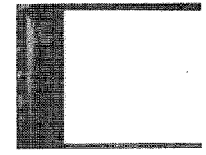 |
| 3: Open 12 of 24 | 4: Open 13 of 24 | 5: Open 14 of 24 | 6: Open 15 of 24 |
| 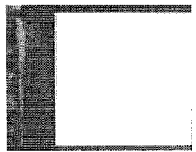 | 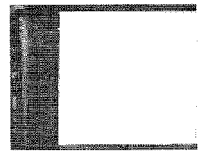 | 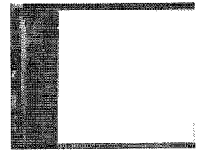 | 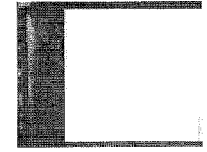 |
| 7: Open 16 of 24 | 8: Open 17 of 24 | 9: Open 18 of 24 | 10: Open 19 of 24 |
| 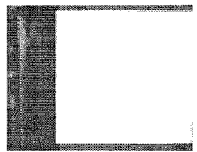 | 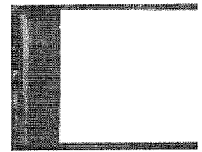 | 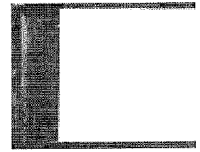 | 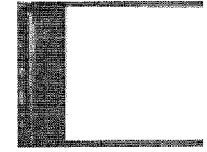 |
| 1: Open 20 of 24 | 2: Open 21 of 24 | 3: Open 22 of 24 | 4: Open 23 of 24 |
| 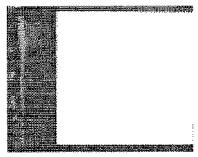 | 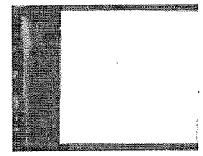 | 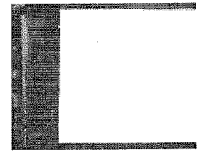 | 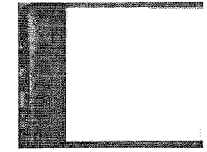 |
FIG. 11a Images: 20080121-181213
5: Open 24 of 24  6: BB 1 of 1  7: Xedge 1 of 1  8: Yedge 1 of 1
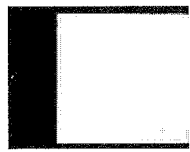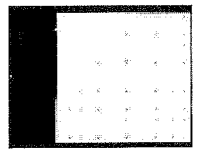
FIG. 11b

Presampling x-MTF: 20080121-181213
Spectrum: RQA-5 (70kV)
Incident exposure: 0.606 mR
Pixel x size in image plane: 0.202 mm
Sampling cut-off frequency: 2.5 cycles/mm
Line-spread-function window width: 20.0 mm
| Freq (cy/mm) | MTF |
|---|---|
| 0.0 | 1.00 |
| 0.5 | 0.83 |
| 1.0 | 0.61 |
| 1.5 | 0.42 |
| 2.0 | 0.27 |
| 2.5 | 0.17 |
| 3.0 | 0.11 |
| 3.5 | 0.07 |
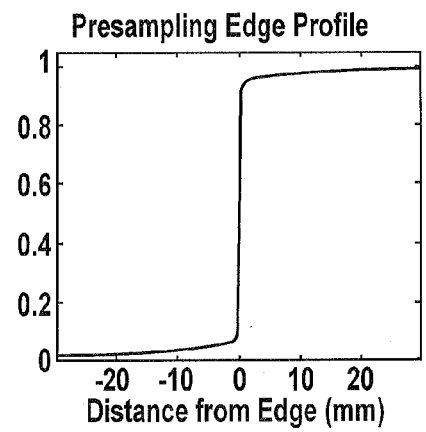
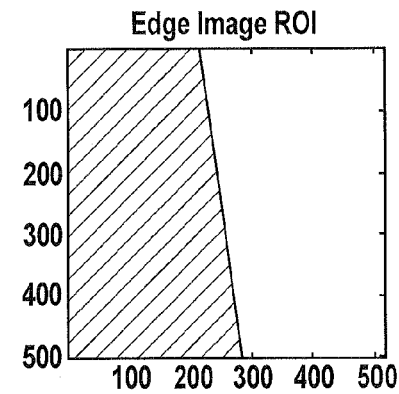
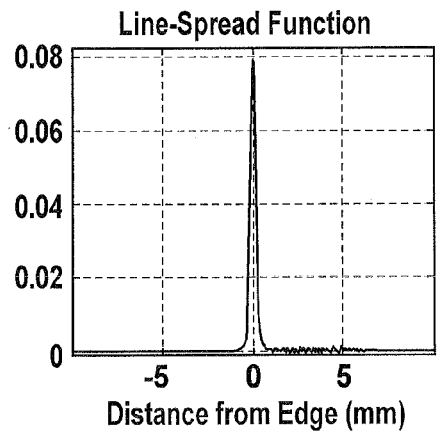
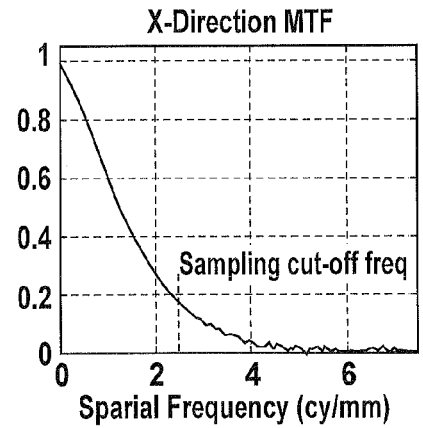
FIG. 11c

APPARATUS FOR ASSISTING DETERMINATION OF DETECTIVE QUANTUM EFFICIENCY

FIELD

The present invention relates generally to ionizing radiation imaging systems and more specifically to an apparatus for assisting determination of detective quantum efficiency (DQE) of x-ray imaging systems.

BACKGROUND

X-ray imaging is the mainstay of diagnostic radiology, with over 20 million radiographic procedures performed in Canada alone each year. Although x-ray technologies have been under development for over 100 years, their cost, use and potential for diagnosis continue to accelerate. Due to the health risks associated with exposure to radiation and the risks due to inconclusive or misleading diagnoses, technical excellence in the design and maintenance of x-ray medical imaging systems is critical to achieving high-quality images and medical care. In x-ray imaging, image quality is a balance between system performance and patient radiation dose. Unfortunately, not all systems—both new and old—provide patients with the benefits of the highest possible image quality consistent with a specified radiation exposure. This is particularly true for some of the emerging lower-cost digital technologies that are beginning to have a substantial impact on the practice of radiology.

The use of sub-optimal equipment has two impacts on patient well being. The first is unnecessary exposures to ionizing radiation. This risk is managed in many jurisdictions across Canada, the US and Europe by implementing maximum allowable exposure levels for standardized radiographic procedures under specified conditions. Of potentially greater risk is that of missed or misleading diagnoses due to suboptimal image quality. Image signal-to-noise ratio (SNR) is related to both x-ray exposure levels and the ability of an imaging system to extract the best possible image SNR from the radiation incident on the imaging detector. A poor image SNR prevents the detection of low-contrast lesions, such as small tumours, and it is therefore critical that x-ray imaging systems be designed and maintained to produce the best possible image SNR consistent with acceptable levels of radiation exposure.

Medical facilities routinely monitor image quality using the best practices and equipment currently available. These include measurements of "line-pair" test objects to determine spatial resolution, low-contrast test objects to determine "detectability," anthropomorphic test phantoms and others. While these are subjective measures with little quantitative value, they are the best presently available and hence are in wide-spread use. In addition, they provide no specific information regarding the "dose efficiency" of the imaging system. Systems with poor dose efficiency may be able to produce high-quality images, but require increasing the radiation dose delivered to the patient. With many of the new digital technologies, it has become even more difficult for equipment users to be aware of these shortcomings. While the onus is on the user to make a wise purchase decision and to ensure proper equipment maintenance, there is no instrumentation available to the non-expert user to assess the performance and dose efficiency of their equipment.

The scientific community has generally adopted use of both the modulation transfer function (MTF) and detective quantum efficiency (DQE) as the most appropriate measures of system performance. The MTF is expressed as a function of spatial frequency and describes spatial resolution. The DQE is also expressed as a function of spatial frequency and is a measure of system "dose efficiency" and therefore risk to the patient. A high-quality imaging system will always have excellent MTF and DQE parameters. The DQE of an ideal system is unity for all spatial frequencies of importance; however, most systems range between 0.1 and 0.5, and all too often even less. The DQE differs from one manufacturer to another, and may vary with system design, exposure level, system age, and level of servicing. Since DQE is inversely proportionate to dose, in many cases by optimizing x-ray parameters, there exist opportunities to achieve patient dose reductions by factors of 2 to 10 without compromising image SNR.

The practical significance of the DQE is generally accepted by major vendors. In the United States, the Food and Drug Administration (FDA) now requires submission of both MTF and DQE documentation before approval is issued for new radiographic devices. However, the FDA does not verify manufacturers' claims and it is up to the end user to ensure acceptability of the equipment. The DQE is thought to be such an important metric by the community in general that standards are being developed by scientists and engineers in both academia and industry around the world, such as Task Group #16 of the American Association of Physicists in Medicine and Working Group 33 of the International Electrotechnical Commission (IEC 62220-1). These standards are attempting to establish consistency in DQE measurements to enable comparisons between different imaging systems and manufacturers and quantitative interpretation of DQE values.

A common expression for DQE as a function of spatial frequency is:

$$DQE(u) = \frac{MTF^2(u)}{XQ_o NPS(u)/d^2} \quad \text{(Equation 1)}$$

where u is spatial frequency, often expressed in units of cycles/mm;

MTF(u) is the measured MTF;

X is the measured incident free-air exposure in Roentgen (R), or air KERMA (kinetic energy released in medium) in Gray (Gy);

$Q_o$ relates the input exposure or air KERMA to an associated number of incident x-ray quanta per $mm^2$;

NPS(u) is the measured Wiener noise power spectrum (NPS), and d is the mean dark-subtracted pixel value in open-field images used to calculate the NPS.

A measurement of the DQE is achieved by determining each of these parameters and solving the above Equation 1.

There are, however, four serious technical issues that restrict widespread use of the DQE, such that measurements are performed only by a few experts, and only in laboratory or special test environments:

1. The first is the time and effort required by a non-expert to acquire the necessary expertise in DQE physics. This includes becoming an expert in x-ray physics, Fourier methods and the theoretical basis of the DQE and measurement techniques.

2. The second is the time and effort required to create and validate a facility to measure the quantities required to calculate the DQE. Guidelines have been established (IEC 62220-1) that help describe how such a facility should be constructed. Great care must be taken to ensure measurements are not subject to inadequate considerations that could result in erroneous DQE results. These include but are not limited to x-ray scatter, poor design of components used in the measurement and inadequate monitoring of x-ray intensity fluctuations.

3. The third is developing the necessary software required to calculate the DQE from acquired images and measured data. Software is freely available to calculate certain components of the DQE, such as the modulation transfer function (MTF), but no validated, readily available software currently exists to complete the DQE calculation.

4. The fourth is that each DQE measuring facility must be validated to ensure accuracy and consistency with other facilities. This validation is very difficult as sites contain different x-ray equipment, and there is no generally accepted test object to calibrate the facility against a standard or enable inter-site comparisons. Rather, validation can only be performed by comparing results obtained using a particular imaging system with results obtained elsewhere using a similar imaging system. A comprehensive validation, under a range of conditions or for new imaging systems is extremely difficult.

U.S. Pat. No. 6,521,886 ("'886"), "Method of monitoring changes in the detective quantum efficiency of an x-ray detector", describes methods and apparatus to allow determination of changes in DQE relative to an initial standard. A "portable" DQE measurement facility involving a working table surface mounted on wheels is described. Some of the equipment required to measure the DQE is contained on the moveable table and can be wheeled out of the way when not in use, reducing the requirement for a dedicated DQE facility. However the system remains very cumbersome, comprising a complete lab bench with wheels. In addition, a trained physicist is still required to measure the DQE using conventional manual instrumentation and techniques. Further, '886 notes that the DQE is proportional to the ratio R(u) where $$R(u) = \frac{MTF^2(u)}{NPS(u)/d^2} \quad \text{(Equation 2)}$$

where MTF(u) is the system MTF expressed as a function of spatial frequency u, d is the average pixel value in an image acquired with a uniform x-ray exposure and NPS(u) is the corresponding image noise-power spectrum at that exposure. Thus, if all other factors remain unchanged, measured changes in either MTF(u) or $NPS(u)/d^2$ may indicate a change in R(u) and therefore a change in DQE. However, no methods are taught in '886 for determination of actual DQE values of the x-ray detector. Rather, methods are restricted to monitoring only time-course changes in the DQE relative to an initial arbitrary reference value obtained on the same unit. While measurement of R(u) is simpler than a measurement of DQE (u) and does not require a DQE measurement facility, it does not allow determination of actual DQE values of an x-ray detector that could be used to compare the performance characteristics of an x-ray imaging system to theoretical expectations, specific industry standards, or to other x-ray imaging systems made by the same or different manufacturers.

SUMMARY

Present embodiments provides a system, apparatus and method for quantitatively determining MTF and/or DQE values of an ionizing radiation imaging detector and/or an imaging system employing ionizing radiation. Determination of the MTF and/or DQE is achieved through measurement instrumentation housed within a self-contained unit plus images acquired by the test system, and software which incorporates the measurements achieved from the instrumentation into an algorithm to determine the MTF and/or DQE. A host computer can be interfaced to the self-contained unit. The self-contained design is internally calibrated and has specific design features to prevent contamination from outside influences, such as ionizing radiation scatter, to ensure accurate MTF and/or DQE measurements. As a result, there is no requirement placed on the user to have specific ionizing radiation or DQE physics expertise, and there is no need for additional validation by the user.

Present embodiments make available, for the first time, a device that can be used to automate the measurement of data and the calculation of the MTF and DQE. Prior to these embodiments, there was no method available anywhere to do this. Specifically:

1. Present embodiments provide a controlled and easily portable environment for the measurement of parameters required to determine the MTF and/or DQE. In particular, the controlled environment enables a true measure of the free-air ionizing radiation exposure incident on the detector without having to remove or dismantle the detector system to achieve a true free-air measurement or to make exposure measurements elsewhere in the ionizing radiation beam with corrections for distance from the detector. In addition, an internal detector monitors each exposure and can be used to compensate for exposure fluctuations as recommended by IEC 62220-1.

2. Present embodiments provide an apparatus that is self contained and internally calibrated to ensure accurate measurement of each parameter. Since all data acquisition (except for images acquired on the system being tested) is internal to the apparatus, and each measurement is made without influence from the surrounding environment, the apparatus enables the direct measurement of MTF and/or DQE without the need for a carefully constructed, calibrated and validated DQE laboratory or test environment.

3. Present embodiments include an automated algorithm for matching measurements of ionizing radiation exposure and other information with the corresponding images acquired by the imaging system. This algorithm uses a statistical approach that minimizes the standard error in time intervals between measured exposures, with time intervals between images measured by the imaging system. This algorithm eliminates the need for internal clocks in the apparatus and/or algorithm to be synchronized with internal clocks in the imaging system. A means is also provided to enable a manual matching of exposures to images as a backup method.

4. Present embodiments provides a mechanism and process to ensure that the ionizing radiation spectrum, such as an x-ray spectrum, used for measuring the DQE conforms to standard spectra described in IEC 62220-1. This process helps automate measurements of the MTF and/or DQE and is included in present embodiments as a convenience to the user for fast MTF and/or DQE measurements.

A first broad aspect of an embodiment seeks to provide an apparatus for assisting determination of at least one of modulation transfer function (MTF) and detective quantum efficiency (DQE) of an ionizing radiation imaging system, the ionizing radiation imaging system including an ionizing radiation detector for detecting an ionizing radiation beam received from an ionizing radiation source. The apparatus comprises a box having two generally aligned windows defining a space there between within the box, each window being generally transparent to ionizing radiation and of an area substantially similar to the ionizing radiation beam such that, when the box is placed in front of the detector, the ionizing radiation beam may substantially pass through the box, including the space, and into the detector. The apparatus further comprises a KERMA (kinetic energy released in medium) module, contained within the box, for measuring at least one of incident free-air exposure and incident free-air KERMA of the ionizing radiation beam when the ionizing radiation beam passes through the space. The apparatus further comprises at least one backscatter baffle for preventing backscatter of the ionizing radiation beam from the detector into the KERMA module, when the KERMA module is in use. The apparatus further comprises at least one scatter baffle for preventing scatter of the ionizing radiation beam within the box into the KERMA module, and to reduce backscatter that may be generated from the backscatter baffle, when the KERMA module is in use. The apparatus further comprises at least one MTF module, contained within the box, for enabling acquisition of at least one edge image by the ionizing radiation imaging system. Each of the KERMA module, the at least one backscatter baffle and the at least one MTF module are independently moveable in and out of the space, such that at least one open image, a dark image, and the at least one edge image may be independently acquired by the ionizing radiation imaging system when the ionizing radiation beam passes through the box, and KERMA module measurements may be performed independent of image acquisition, such that the images and the KERMA module measurements may be processed to determine DQE. The apparatus further comprises an interface for acquiring data from the KERMA module, and for controlling moving of each the KERMA module, the at least one backscatter baffle, and the at least one MTF module in and out of the space.

In some embodiments of the first broad aspect, the apparatus further comprises at least one monitor ionizing radiation detector within the box, enabled to engage the ionizing radiation beam and produce a signal proportional to at least one of the incident ionizing radiation exposure and KERMA, the interface enabled for acquiring data from the at least one monitor ionizing radiation detector.

In other embodiments of the first broad aspect, each window comprises a sheet of an ionizing-radiation transparent material covering an aperture in the box.

In further embodiments of the first broad aspect, the KERMA module comprises a sheet of ionizing radiation absorbing material and an ionization chamber residing substantially in an aperture through the sheet of ionizing radiation absorbing material. In some of these embodiments, the at least one scatter baffle comprises the sheet of ionizing radiation absorbing material of the KERMA module. In some of these embodiments, the apparatus further comprises a plurality of scatter baffles, the plurality of scatter baffles comprising the at least one scatter baffle and sheets of ionizing radiation absorbing material arranged adjacent to each of the windows.

In yet further embodiments of the first broad aspect, the apparatus further comprises at least one of an electrometer and current amplifier in communication with the ionization chamber.

In some embodiments of the first broad aspect, the at least one backscatter baffle is enabled to reside between the KERMA module and a detector facing side of the box, when the KERMA module is in use, such that ionizing radiation passing through the KERMA module is generally absorbed by the backscatter baffle. In some of these embodiments the at least one backscatter baffle comprises the at least one MTF module.

In other embodiments of the first broad aspect, the apparatus further comprises a temperature measuring device in communication with the interface for measuring the temperature inside the box, such that measurements of DQE may be temperature corrected.

In further embodiments of the first broad aspect, the apparatus further comprises a pressure measuring device in communication with the interface for measuring the pressure inside the box, such that measurements of DQE may be pressure corrected.

In yet further embodiments of the first broad aspect, the apparatus further comprises at least one motion control unit for moving each of the KERMA module, the at least one backscatter baffle, and the at least one MTF module in and out of the space. In some of these embodiments, the at least one motion control unit comprises at least one of a slideable apparatus, a pivotable apparatus, and a rotatable apparatus. In other embodiments, the at least one motion control unit comprises a motor in communication with the interface, the motor for moving of each the KERMA module, the at least one backscatter baffle, and the at least one MTF module in and out of the space. In further embodiments, the interface comprises a manual interface for manually controlling the at least one motion control unit.

In some embodiments of the first broad aspect, the apparatus further comprises a geometric correction module for enabling acquisition of at least one geometric correction image by the ionizing radiation imaging system, the at least one geometric correction image for determining geometric correction coefficients that enable a "de-warping" algorithm used in the correction of image geometric distortions, the geometric correction module being independently moveable in and out of the space such that the geometric correction image may be acquired independent of the at least one open image, the dark image, the at least one edge image and the KERMA module measurements.

In other embodiments of the first broad aspect, the at least one MTF module comprises an area that generally absorbs ionizing radiation and an area that is generally transparent to ionizing radiation, wherein the intersection of each of the areas defines at least one of an edge in an x-direction and an edge in a y-direction.

In further embodiments of the first broad aspect, the at least one MTF module is enabled to move through the space during the acquisition of the at least one edge image to enable measurement of an MTF that is at least one of motion dependent and time dependent.

In further embodiments of the first broad aspect, the ionizing radiation comprises at least one of x-rays and gamma radiation.

In yet further embodiments of the first broad aspect, the ionizing radiation imaging system comprises at least one of a computed-tomography system, a fluoroscopy system, a mammography imaging system, a dental imaging system, a veterinary imaging system, and a nuclear medicine imaging system.

In some embodiments of the first broad aspect, the ionizing radiation detector comprises at least one of a digital detector, a flat-panel detector, a computed radiography (CR) detector, a film detector, a phosphor-based detector, a semi-conductor-based detector, an image-intensifier-based detector, an x-ray detector and a gamma radiation detector.

A second broad aspect of an embodiment seeks to provide a system for determining at least one of modulation transfer function (MTF) and detective quantum efficiency (DQE) of an ionizing radiation imaging system. The system comprises the apparatus of the first broad aspect. The system further comprises a computing device enabled to receive the at least one open image, the dark image, the at least one edge image, and the KERMA module measurements. The computing device comprises a memory for storing the at least one open image, the dark image, the at least one edge image, the KERMA module measurements. The DQE determination software is enabled for determining at least one of incident free-air exposure and incident free-air KERMA of the ionizing radiation beam at an image plane of the detector, based on the KERMA module measurements and distance between the KERMA module and the image plane. The DQE determination software is further enabled for determining the MTF of the imaging system by processing the at least one open image, the dark image, and the at least one edge image. The DQE determination software is further enabled for determining a noise power spectrum (NPS) of the imaging system by processing the at least one open image and the dark image. The DQE determination software is further enabled for determining an average pixel value of the at least one open image by processing the at least one open image and the dark image. The DQE determination software is further enabled for determining the number of ionizing radiation photons per unit area and exposure (Qo). The DQE determination software is further enabled for determining DQE of the image system by processing the at least one of incident free-air exposure and incident free-air KERMA of the ionizing radiation beam at the image plane of the detector, the MTF, the NPS, the average pixel value and the Qo. The computing device further comprises a processor for processing the DQE determination application.

BRIEF DESCRIPTIONS OF THE DRAWINGS

Embodiments are described with reference to the following figures, in which:

FIGS. 11a to 11f depicts reports generated using an apparatus for assisting determination of detective quantum efficiency (DQE) of an x-ray imaging system, according to a non-limiting embodiment.

DETAILED DESCRIPTION OF THE EMBODIMENTS

Figure 1:
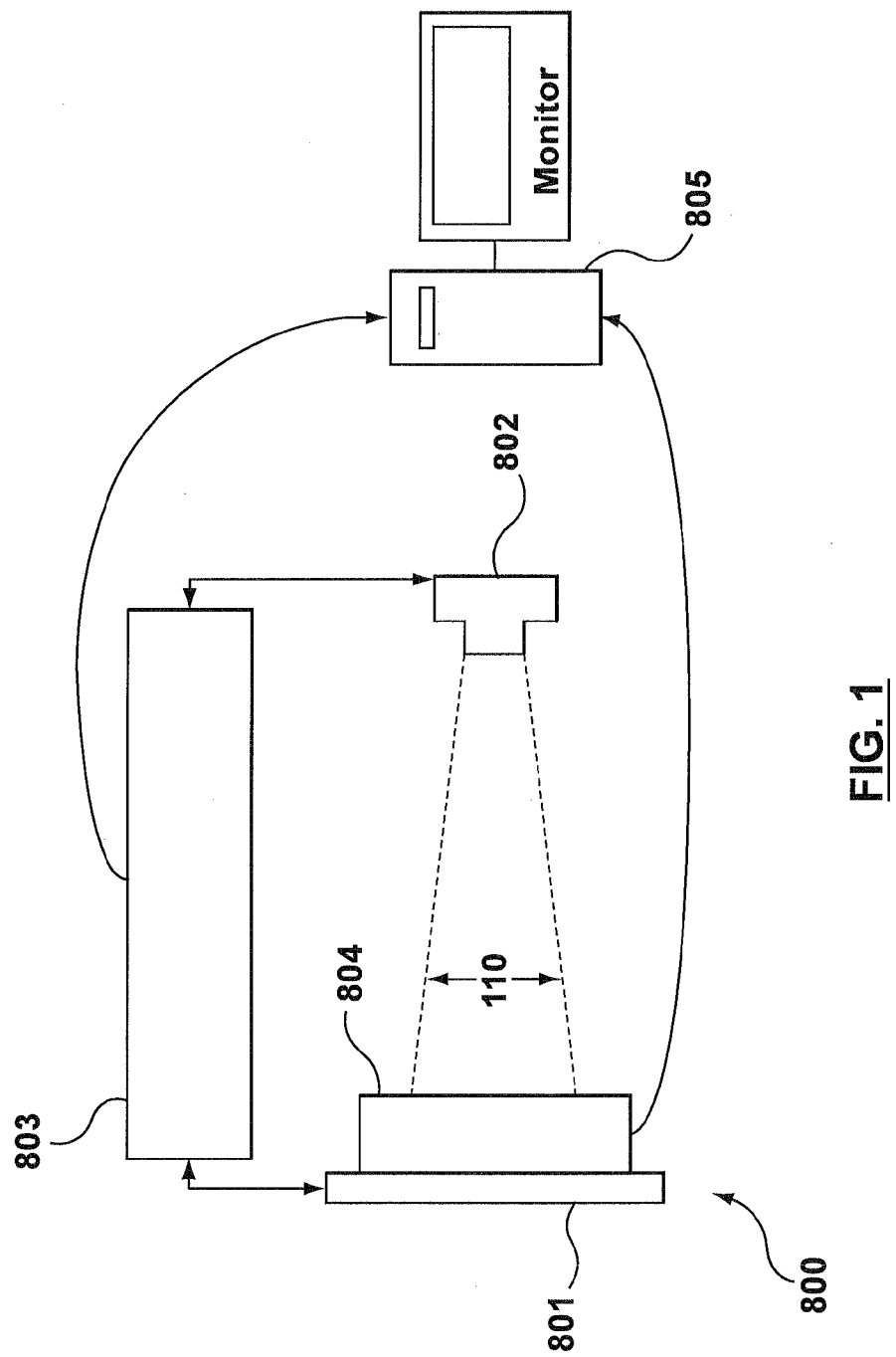
FIG. 1 depicts a system for determination of detective quantum efficiency (DQE) of an x-ray imaging system, according to a non-limiting embodiment.

While embodiments described herein are with reference to imaging systems using x-rays, it is understood that apparatus and methods described herein may be directed to any imaging system using ionizing radiation. Hence, FIG. 1 depicts a system 800 for determination of detective quantum efficiency (DQE) of an x-ray imaging system, according to a non-limiting embodiment. The x-ray imaging system generally comprises an x-ray detector 801. The detector 801 is generally enabled for detecting an x-ray beam received from an x-ray source 802, the source 802 enabled to emit an x-ray beam 110 into the detector 801, such that the x-ray beam 110 passes through objects placed between the detector 801 and the source 802. Hence, images of the objects may be acquired by processing x-rays detected at the detector 801 via an image generation device 803. In general the detector 801, the source 802 and the image generation device 803 are known to a person of skill in the art.

The system 800 generally comprises an apparatus 804 for assisting determination of detective quantum efficiency (DQE) of the x-ray imaging system and a computing device 805. The computing device 805 is in communication with the apparatus 804 via any suitable wired or wireless connection, and/or a suitable communications network, such as a local area network (LAN). In general, the apparatus 804 is further configured to receive images from the image generation device 803, via either a connection similar to the connection with apparatus 804, or by transfer of image files via any suitable medium, including CD-ROM, flash drives, magnetic media and the like. In these embodiments, image files are saved onto the suitable medium at the image generation device 803 and manually transferred to the computing device 805.

The computing device 805 is enabled to process data acquired from the apparatus 804 and the imaging generation device 803, including image files, to determine DQE of the x-ray imaging system. With brief reference to FIG. 7, the computing device 805 generally comprises a memory 730 for storing DQE determination software 740, and a processor 720 for processing the DQE determination software and data acquired from the apparatus 804 and the imaging generation device 803.

The apparatus 804 is enabled to measure the incident free-air exposure and/or the incident free-air KERMA, and modifying the pattern of x-rays that reach the detector 801 to assist in determining DQE parameters, in a manner which is described below.

Figure 2:
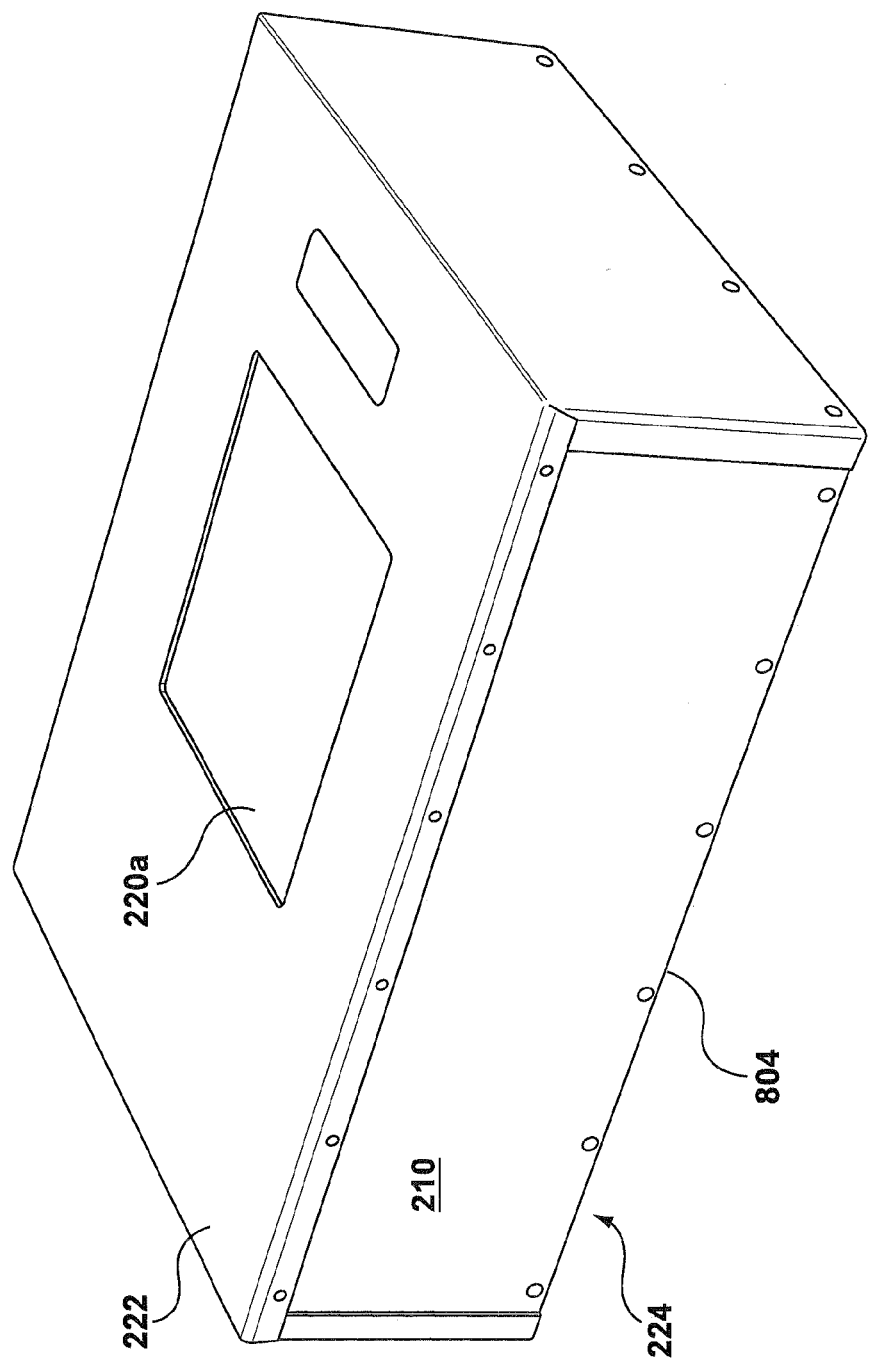
FIG. 2 depicts a perspective view of an apparatus for assisting determination of detective quantum efficiency (DQE) of an x-ray imaging system, according to a non-limiting embodiment.
Figure 3:
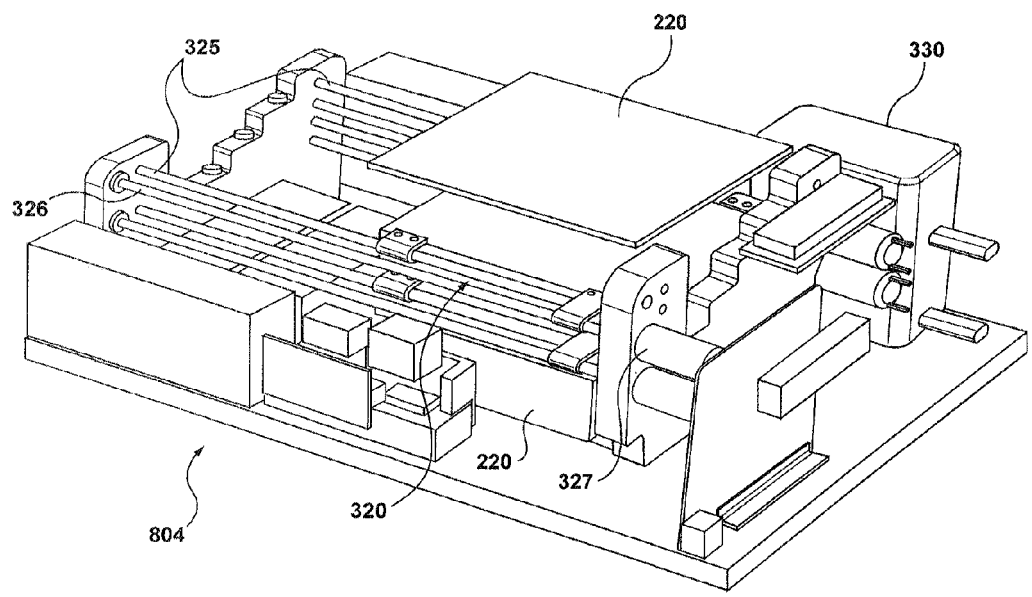
FIG. 3 depicts a perspective view of the interior of an apparatus for assisting determination of detective quantum efficiency (DQE) of an x-ray imaging system, according to a non-limiting embodiment.

Attention is now to FIGS. 2 and 3, which depict the apparatus 804 for assisting determination of detective quantum efficiency (DQE) of an x-ray imaging system, according to a non-limiting embodiment. FIG. 2 depicts a perspective view of the apparatus 804, while FIG. 3 depicts a perspective view of components internal to the apparatus 804, each according to a non-limiting embodiment. The apparatus 804 generally comprises a box 210 having two generally opposed and aligned windows 220a and 220b (generically a window 220, and collectively windows 220), defining a space there between within the box 210, the windows 210 being generally transparent to x-rays and of an area substantially similar to the x-ray beam 110 at the detector 801. While only one such window 220a, located at a source facing surface 222 of the box 210, is visible in FIG. 2, it is understood that a second such window 220b (visible in FIG. 3) is located at a detector facing surface 224 of the box 210, generally parallel to the source facing surface 222. Hence when the box 210 is placed in front of the detector 801, as in FIG. 1, an x-ray beam (such as x-ray beam 110) may pass into the box 210 via the window 220a, and out of the box 210 via the window 220b and into the detector 801. In one non-limiting embodiment, each window 220 comprises of a cover (for example see FIG. 6) which covers an aperture in each surface 222 and 224, the cover comprised of a material which is generally transparent to x-rays. In a non-limiting embodiment, the cover is comprised of carbon fiber, however that any suitable material that is transparent to x-rays is within the scope of present embodiments. Further, the cover is of a thickness suitable for enabling transparency or near-transparency of x-rays and for providing suitable structural rigidity. In other embodiments, each window 220 may comprise a sheet of a material similar to the cover, which resides within the box 210 (e.g. on an interior side of each surface 222 and 224, covering an aperture in each surface 222 and 224) or integrated into each surface 222 and 224, as desired.

In some embodiments, the box 210 may be comprised of a suitable x-ray absorbing material. In other embodiments, the box 210 may be lined with sheets of a suitable x-ray absorbing material, such as scatter baffles 620 described below with reference to FIG. 6. In any event, apart from the aligned windows 220, x-rays are generally absorbed when they impinge upon the box 210 to the extent that scattered x rays are not incident on an ionization chamber 507 described below, or pass through the window 220b.

When the box 210 (i.e. apparatus 804) is placed between the source 802 and the detector 801, an x-ray beam may pass through the box 210 by passing through the aligned windows 220. This is further illustrated in FIG. 4, which depicts a successful non-limiting prototype of the apparatus 804 in place in front of the detector 801. The x-ray beam 110 is represented by the area 410. In some embodiments, the box 210 is of a size and shape that enables the window 220a to be visible to the x-ray beam 110 when the box 210 is placed in front of the detector 801, while in other embodiments, a mounting apparatus (not depicted) may be used to mount the box 210 in front of the detector 801 in a manner that enables the window 220a to be visible to the x-ray beam 110.

Returning to FIG. 3, inside the apparatus 804 (i.e. inside the box 210) are various modules for enabling assisting determination of detective quantum efficiency (DQE) of an x-ray imaging system. While not all modules are visible in FIG. 3, details of the modules are discussed below. In general, each module is independently moveable in and out of an x-ray beam passing through the box 210, i.e. independently moveable in and out of the space between the aligned windows 220, such that each module may engage an x-ray beam entering the box 210 via the window 220a, each module being generally parallel to the aligned windows 220 when in use.

For example, in one non-limiting embodiment, a module (such as a KERMA module 503, described below) may be mounted on a motion control unit 320, as depicted in FIG. 3. In this embodiment, the motion control unit 320 comprises a slideable apparatus, which in turn comprises a pair of rails 325 and a screw device 326 attached to a motor 327, the motor for turning the screw device 326. The rails 325 are of a length that enables the module to slide between the aligned windows 220, and out from between the aligned windows 220 when the motor 327 is activated to turn the screw device 326. Hence, in this embodiment, there is a space adjacent the space between the aligned windows 220 where the module resides while not in use (i.e. when the module is not engaging an x-ray beam entering the window 220a), the box 210 being of a suitable size and shape to encompass this space, and to contain the module in this space, when the module is not in use.

Figure 5:
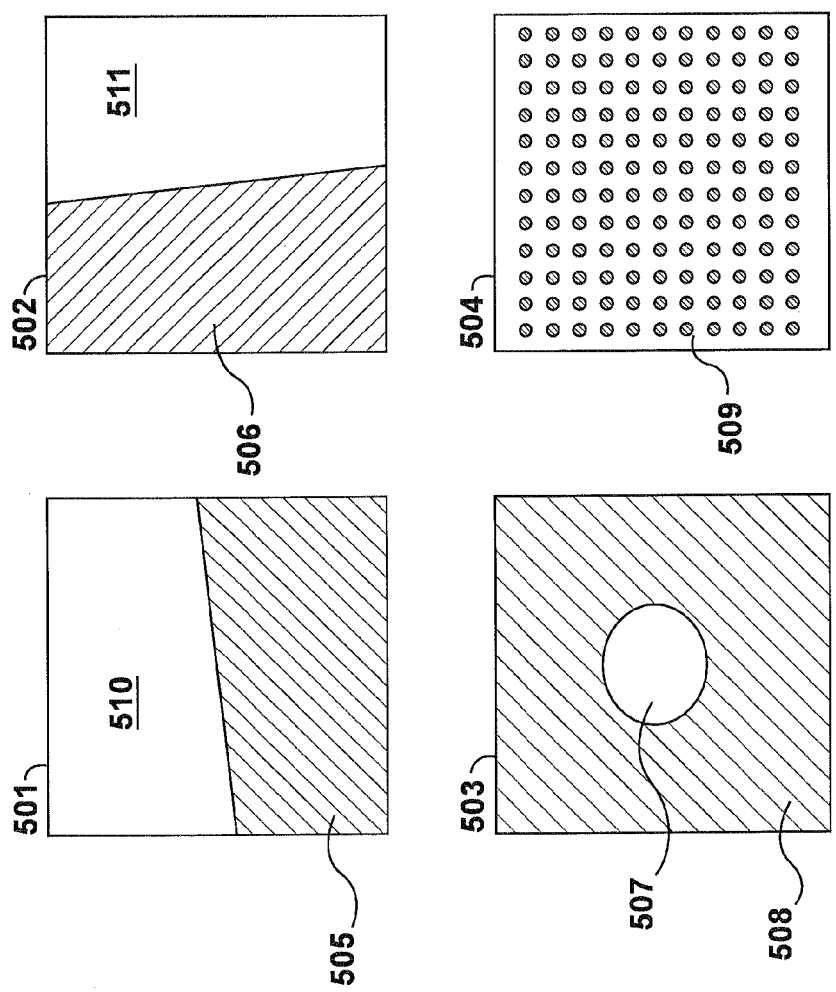
FIG. 5 depicts modules used in an apparatus for assisting determination of detective quantum efficiency (DQE) of an x-ray imaging system, according to a non-limiting embodiment.

The embodiment depicted in FIG. 3 comprises up to four modules (e.g. as depicted in FIG. 5) in a stack, each module mounted to a pair of rails similar to the rails 325, and associated screw devices and motors, as described above. However, other embodiments may comprise fewer than four modules, while other embodiments may comprise greater than four modules. For space considerations, the motors and associated screw devices are distributed two a side. The modules are generally independently moveable, parallel to one another, and spaced within the stack to enable such moveability. It may be desirable in some embodiments, for certain modules to be positioned within the stack closer to or further away from each of the windows 220a and 220b, however this will be described in further detail below.

In another non-limiting embodiment, the motion control unit 320 may comprise a pivotable apparatus (not depicted) for moving a module in and out of the space between the aligned windows 220. For example, each module may be attached to the pivotable apparatus via a hinge, and the pivotable apparatus may be activated (e.g. via a motor) to pivot the module in and out of the space between the aligned windows 220. When the module is in use, the module will reside between the aligned windows 220, and is generally parallel to the aligned windows 220. However, when not in use, the module may be generally perpendicular to the aligned windows 220, having been pivoted out of the space between the aligned windows 220 via the hinge. In these embodiments, the box 210 is of a suitable size and shape to enable the module to pivot in and out of the space between the aligned windows 220. A pivotable apparatus further enables the distance between the module and each window 220 to be controlled. For example, in some embodiments it may be desired that a module reside very near to one of the windows 220, when in use. Hence the hinge may be positioned near an edge of a desired window 220, such that when the module is pivoted into place, the module resides very near to the desired window 220.

In yet further embodiments, the motion control unit 320 may comprise a rotatable apparatus (not depicted), such as a carousel, for moving a module in and out of the space between the aligned windows 220.

In yet further embodiments, the apparatus 804 may comprise any suitable combination of sliding apparatuses pivotable apparatuses and rotatable apparatuses to independently move modules in and out of the space between the aligned windows 220, with some modules being slideable other modules being pivotable and yet further modules being rotatable in and out of the space between the aligned windows 220. Furthermore, in other embodiments, the apparatus for moving the modules in and out of the space between the aligned windows 220 may not be motorized, but rather may be manually operated, for example the interface 330 comprising a manual interface with the apparatus for moving the modules in and out of the space between the aligned windows 220.

Hence, the apparatus 804 further comprises an interface 330 (for example see element 330 of FIG. 3, further described with reference to FIG. 7 below) for acquiring data from the KERMA module (described below), monitor x-ray detectors (described below), if present, and for controlling moving of each module relative to the space between the aligned windows 220. For example, the apparatus 804 may be in communication with the computing device 805 via the interface 330, and may receive signals from the computing device 805 indicating which module is to be moved into the space between the aligned windows 220, and which modules are to be removed from the space between the aligned windows 220. The interface 330 may then convey signals to the motors to control the position of the modules.

FIG. 5 depicts non-limiting embodiments of modules 501, 502, 503 and 504, each module for assisting in the determination of detective quantum efficiency (DQE) of an x-ray imaging system, which are located within the apparatus 804 (i.e. contained within the box 210) each module 501, 502, 503 and 504 being independently moveable in and out of the space between the aligned windows 220, as described above.

The module 501 comprises an x-edge MTF module, which comprises an area 505 which is not transparent to x-rays (e.g. x-rays entering the area 505 are generally absorbed) and an area 510 which is generally transparent to x-rays. The intersection of the area 505 and the area 510 generally defines an "x-edge" which is nearly perpendicular to the x direction, for example 1 to 4 degrees from perpendicular. The area 505 generally comprises a material and a thickness which absorbs x-rays, such that when the module 501 is moved between the aligned windows 220, and when x-rays are passing through the aligned regions (e.g. when the apparatus 804 is in use as in FIGS. 1 and 4), the detector 801 may acquire an image of the x-edge which assists in the determination of the x-direction MTF, as described below. In one non-limiting embodiment, area 505 generally comprises tungsten of a suitable thickness, the "x-edge" of which has been machined to a tolerance suitable for assisting in the determination of the MTF. However, any suitable x-ray absorbing materials may be used, including but not limited to lead.

The module 502 comprises a y-edge MTF module, which comprises an area 506 which is not transparent to x-rays and an area 511 which is generally transparent to x-rays. The module 502 is similar to the module 501 as described above, however module 502 is generally perpendicular to the module 501 such that the intersection of the area 506 and the area 511 generally defines an "y-edge" which is near to perpendicular to the y direction, for example 1 to 4 degrees from perpendicular. Hence, the detector 801 may acquire an image of the y-edge which assists in the determination of the y-direction MTF, as described below.

In some embodiments, the apparatus 804 comprises one MTF module, similar to the module 501, which may be used to acquire images of an x-edge and a y-edge, which assists in the determination of the MTF, the MTF module being rotatable about a central axis from an "x-edge" position (i.e. similar to orientation of the module 501) to a "y-edge" position (i.e. similar to orientation of the module 502).

For example, such an MTF module may comprise an x-ray absorbing material having square/rectangular hole there through, or a square/rectangle of an x-ray absorbing material mounted on an x-ray transparent material.

In another embodiment, there may be only one MTF module in a fixed orientation, such that MTF may be measured in only one direction, with the MTF in the perpendicular direction obtained by rotating the box 210 90 degrees and repeating the measurement process.

In some embodiments, it may be desirable that when an MTF module is in use, the MTF module reside as close as possible to the window 220b, and hence to the detector 801, to minimize the influence of penumbral blur due to finite focal-spot size, as known to one of skill in the art. Off-focal radiation from the x-ray tube in the x-ray source 802, and scatter from aluminum or other materials placed in the x-ray path to harden the beam may also increase penumbral blur. Hence, in these embodiments, it may be desirable that the position of an MTF module be controlled via a pivotable apparatus as described above.

In an alternative embodiment, at least one MTF module may be enabled to moving through the space between the aligned windows 220 during an MTF measurement, in order to obtain a measure of temporal MTF and/or spatiotemporal MTF, or other types of MTF that are motion and/or time dependent. This measure of MTF that are motion and/or time dependent may be useful in applications such as fluoroscopy, and to determine the DQE of fluoroscopic imaging systems. Such movement may be accomplished via a slideable apparatus and/or a slideable apparatus in combination with a pivotable apparatus and/or a rotatable apparatus as described above.

Figure 4:
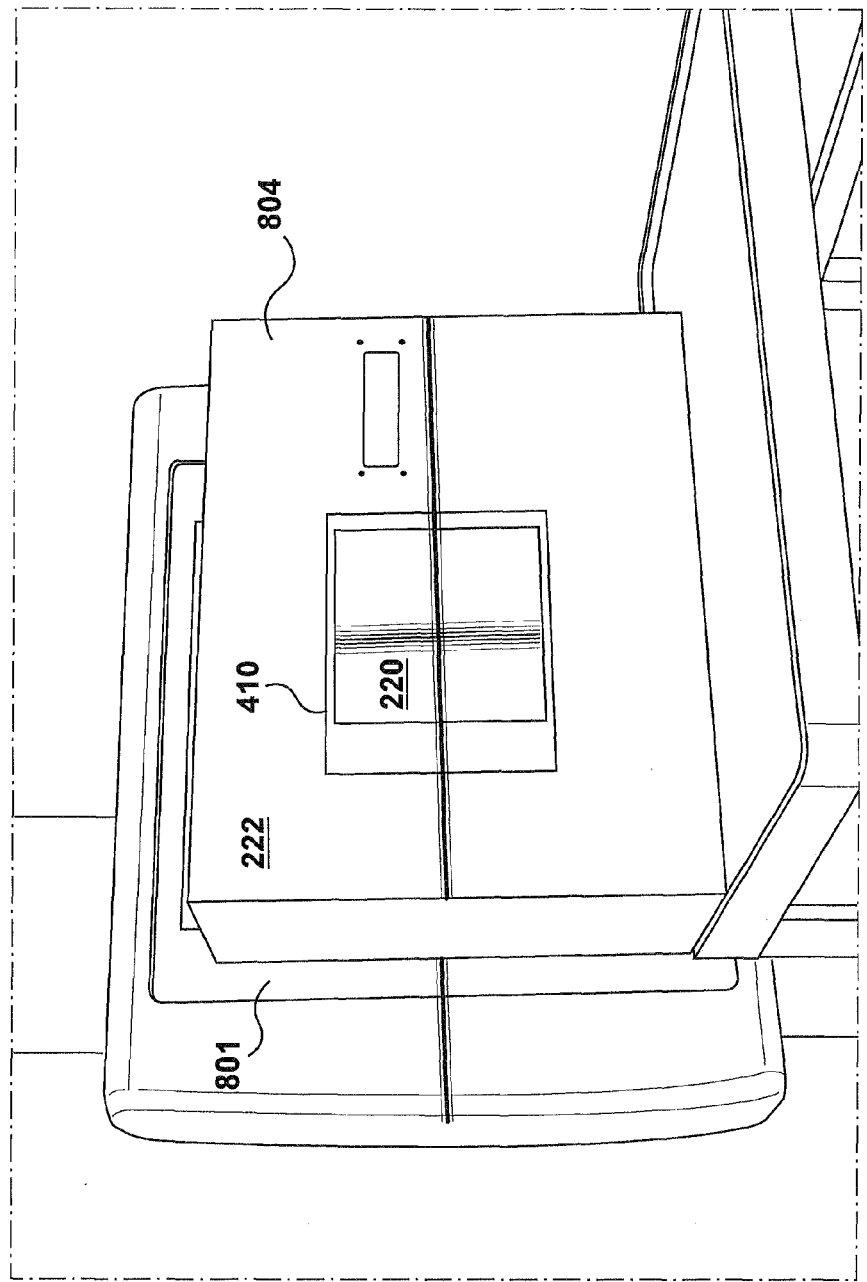
FIG. 4 depicts an apparatus for assisting determination of detective quantum efficiency (DQE) of an x-ray imaging system, in an x-ray beam in front of a detector of an imaging system being tested, according to a non-limiting embodiment.

The module 503 generally comprises a KERMA module for measuring at least one of incident free-air exposure and incident free-air KERMA of an x-ray beam, for example when the box 210 is placed between the source 802 and the detector 801, as in FIGS. 1 and 4. The module 503 generally comprises a sheet 508 of a suitable x-ray absorbing material (including but not limited to tungsten and lead), having an aperture there through, and an ionizing chamber 507, located within the aperture. Ionizing chambers are known to persons skilled in the art, and any suitable ionizing chamber is within the scope of present embodiments. In general, the ionizing chamber 507 will yield a signal that is generally indicative of incident free-air exposure and incident free-air KERMA of an x-ray beam passing through the chamber, for example when the apparatus 804 is in use, as in FIGS. 1 and 4, and the module 503 has been moved between the aligned windows 220. For example, the ionization chamber 507 is generally in communication with an electrometer and/or current amplifier which amplifies the electrical current produced by the ionization chamber 507 when a bias voltage is applied across the ionization chamber 507. The electrometer may be either internal or external to the apparatus 804 and is in communication with the interface 330 such that data may be acquired from the module 503 and at least one of incident free-air exposure and incident free-air KERMA of an x-ray beam may be measured. In some embodiments the electrometer is in communication with the interface 330 via an amplifier and an analog to digital converter.

The module 504 generally comprises a ball bearing (BB) module: beads of x-ray attenuating material, such as ball bearings 509, are suspended in a grid pattern within a material which is x-ray transparent. Any suitable x-ray attenuating material may be used for the ball bearings 509, including but not limited to stainless steel, lead and tungsten. They may be spherical or other shape. The module 504 is generally used to determine geometric correction coefficients that enable a "de-warping" algorithm used in the correction of image geometric distortions and to determine the physical size of detector elements in detector 801. The use of the module 504 is described below.

Figure 6:
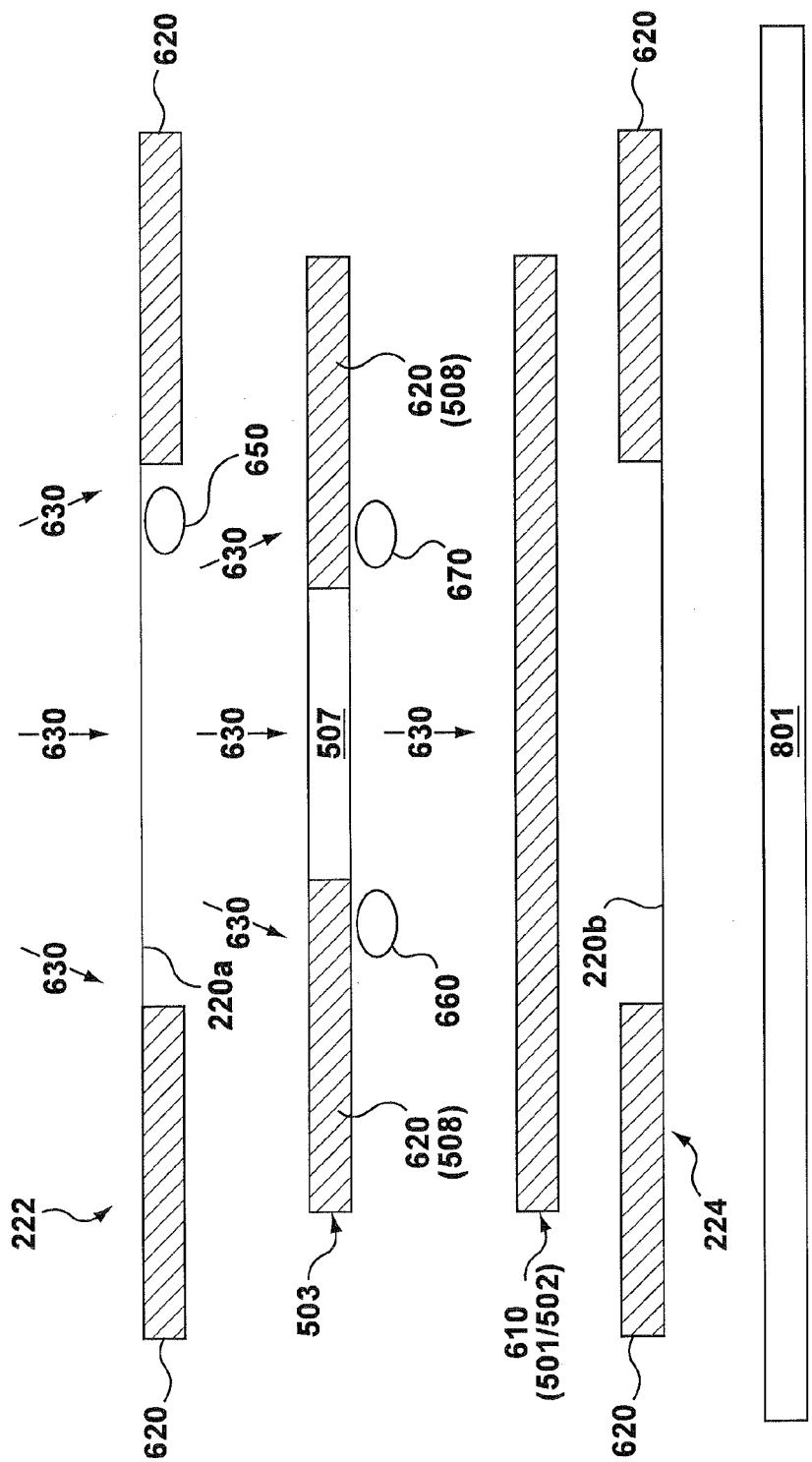
FIG. 6 depicts a cross-sectional schematic diagram of an apparatus for assisting determination of detective quantum efficiency (DQE) of an x-ray imaging system, according to a non-limiting embodiment.

Attention is now directed to FIG. 6 which depicts a cross-sectional schematic diagram of apparatus 804, including the KERMA module (module 503) in operation within the box 210. The x-ray beam is represented by lines 630. FIG. 6 generally depicts the situation depicted in FIGS. 1 and 4, in which the apparatus has been placed in front of the detector 801, and is being exposed to x-rays 630, for example by exposure to the x-ray beam 110, and the KERMA module has been moved into the space between the aligned windows 220 to perform a measurement of at least one of incident free-air exposure and incident free-air KERMA.

From FIG. 6 it is seen that the apparatus 804 also comprises at least one backscatter baffle 610 for preventing the x-ray beam 630 from being incident on the detector 801 and hence prevent backscatter of the x-ray beam from the detector 801 into the KERMA module, when the KERMA module is use, and at least one scatter baffle 620 for preventing scatter of the x-ray beam within the box 210 into the KERMA module, when the KERMA module is use.

The at least one backscatter baffle 610 generally comprises a layer of x-ray absorbing material (including but not limited to lead and tungsten) which fully attenuates the x-ray beam after it passes through the ionization chamber 507, and prevents any straight-line return path from the detector 801 to the KERMA module. This ensures KERMA measurements are not contaminated by backscatter from the detector 801. The at least one backscatter baffle 610 is also independently moveable in and out of the space between the aligned windows 220, such that the at least one backscatter baffle 610 resides between the window 220b and the KERMA module during KERMA measurements, but may be removed for other measurements. In some embodiments, the at least one backscatter baffle 610 may comprise a module distinct from the modules described above, with distinct motion control unit. However in other embodiments, the at least one backscatter baffle may comprise the module 501 and/or the module 502 such that the sheet 508 and/or the area 505 and/or the area 506, respectively, reside between the window 220b and the KERMA module during KERMA measurement preventing any straight-line path from the window 220a to the detector 801. This may be desired to reduce the equipment located within the box 210. As has been described, the interface 330 is enabled for acquiring data from the KERMA module, and for controlling moving of each module, in and out of said space. In embodiments which include a distinct module for the backscatter baffle, the interface 330 is further enabled for controlling moving of the distinct module.

In general, the at least one backscatter baffle 610 and the ionization chamber 507 of the KERMA module are as far apart as possible within the box 210, for preventing radiation emitted from the backscatter baffle 610 from entering the ionization chamber 507. In some embodiments, the distance between the at least one backscatter baffle 610 and the ionization chamber 507 is approximately 10 cm, however other distances may be sufficient for preventing radiation emitted from the backscatter baffle 610 from entering the ionization chamber 507.

The at least one scatter baffle 620 generally comprises the sheet 508 of the module 503, the sheet 508 generally surrounding the ionization chamber 507, and prevents x-rays 630 from being scattered into the ionization chamber 507. In some embodiments, the at least one scatter baffle 620 further comprises sheets of x-ray absorbing material (including but not limited to lead and tungsten) which fully attenuates the x-ray beam in sheets arranged adjacent to each of said windows 220. These additional scatter baffles 620 provide additional absorption of x-rays within the box 210. These additional scatter baffles 620 further prevent any larger-than needed x-ray beam from causing undesired scatter in the box 210.

FIG. 6 also depicts a non-limiting embodiment of the apparatus 804 which comprises an optional at least one monitor x-ray detector 650, in communication with the interface 330.

The at least one monitor x-ray detector 650 generally comprises a solid state detector, such as a silicon based detector, as known to persons of skill in the art. The at least one monitor x-ray detector 650 is generally enabled to engage the x-ray beam and produce a signal proportional to at least one of the incident x-ray exposure and KERMA of the x-ray beam, the interface 330 enabled for acquiring data from the at least one monitor x-ray detector 650. The at least one monitor x-ray detector 650 may be used to monitor fluctuations in the x-ray beam, such that measurements of DQE may be adjusted based on measured fluctuations. Hence, the at least one monitor x-ray detector 650 is generally positioned within the window 220a, but in a manner that does not interfere with x-rays impinging on the ionization chamber 507 or the detector 801.

In some embodiments, the apparatus 804 comprises two or more monitor x-ray detectors 650 disposed around the window 220a such that the x-ray beam entering the window 220a may be detected, mounted in a manner that does not interfere with x-rays impinging on the ionization chamber 507 or the detector 801. For example, if the box 210 is placed in front of the detector 801, as in FIGS. 1 and 4, but the windows 220 are generally misaligned with the x-ray beam such that only a portion of the x-ray beam enters the window 220a, one x-ray detector will produce a higher signal than a second x-ray detector. Hence, the difference in signals may be monitored, for example via the interface 330, to determine misalignment.

In another embodiment, a first monitor x-ray detector 650 is located close to the edge of the window 220a, while a second monitor x-ray detector 650 is located closer into the path of the x-ray beam, in the same plane as the first monitor x-ray detector 650, both mounted in a manner that does not interfere with x-rays impinging on the ionization chamber 507 or the detector 801. The first monitor x-ray detector 650 may be used to monitor whether the edge of the x-ray beam is close to the edge of the window 220a, hence ensuring that the second monitor x-ray detector 650 is covered by the x-ray beam and hence ensuring a robust measurement of to at least one of the incident x-ray exposure and KERMA of the x-ray beam, by the second detector 650.

FIG. 6 also depicts a non-limiting embodiment of the apparatus 804 which comprises an optional temperature measuring device 660 in communication with the interface 330 for measuring the air temperature inside the box 210, such that measurements of exposure or KERMA may be temperature corrected. For example, due to the presence of electronic and electrical equipment inside the box 210, in some embodiments, the temperature in the box 210 may change over time. This can affect the measurements at the ionization chamber 507, for example. However, if the temperature is known, the measurements at the ionization chamber 507 may be corrected using algorithms known to persons of skill in the art. In some embodiments, it is hence desirable that the temperature measuring device 660 be located adjacent the ionization chamber 507.

FIG. 6 also depicts a non-limiting embodiment of the apparatus 804 which comprises an optional pressure measuring device 670 in communication with the interface 330 for measuring the air pressure inside the box 210, such that measurements of exposure or KERMA may be pressure corrected. For example, atmospheric pressure, may affect the performance of the ionization chamber 507. However, if the air pressure at the time of measurement is known, the measurements at the ionization chamber 507 may be corrected using algorithms known to persons of skill in the art. In some embodiments, it is hence desirable that the pressure measuring device 670 be located adjacent to the ionization chamber 507.

Figure 7:
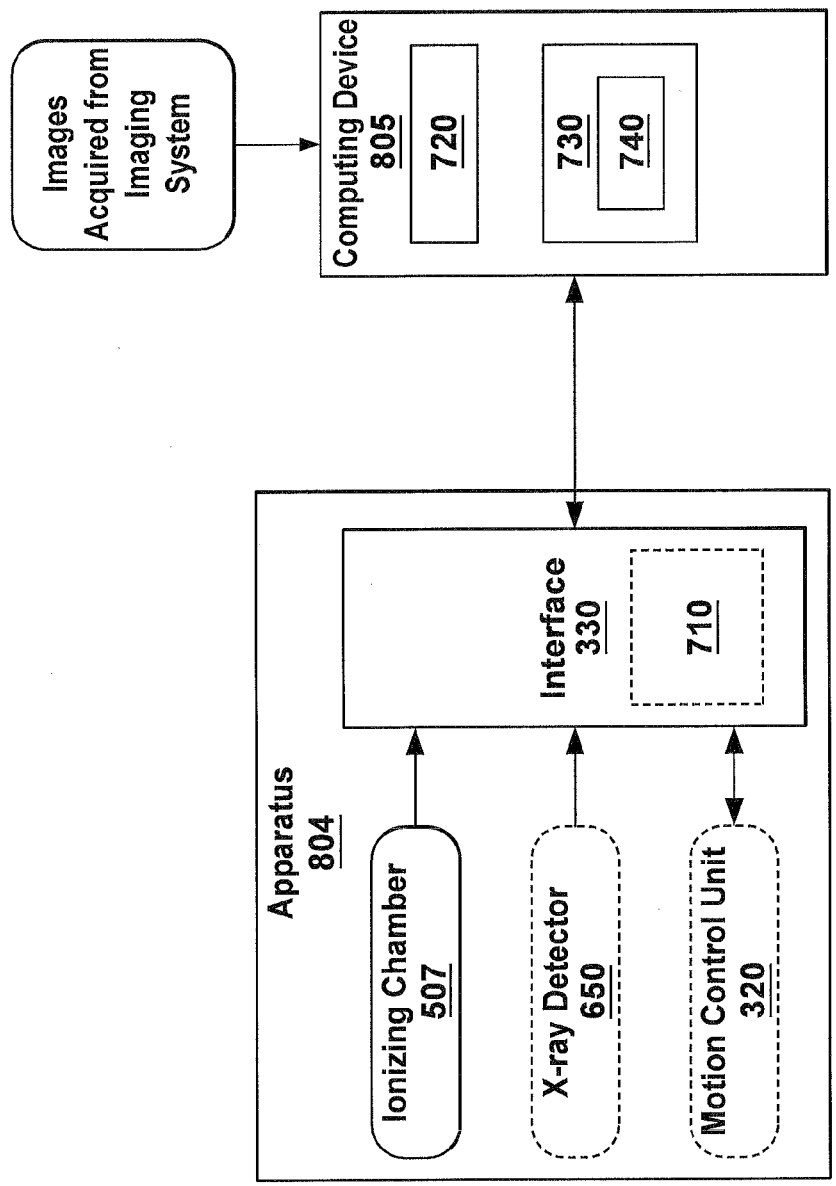
FIG. 7 depicts a block diagram of an apparatus for assisting determination of detective quantum efficiency (DQE) of an x-ray imaging system, according to a non-limiting embodiment.

Attention is now directed to FIG. 7, which depicts a block diagram of apparatus 804 within the system 800 of FIG. 1, according to a non-limiting embodiment. The interface 330 is in communication with the ionizing chamber 507 (e.g. the electrometer and/or current amplifier of the ionizing chamber 507), the at least one monitor x-ray detector 650, if present, and the motion control unit 320. The interface 330 is also in communication with the temperature measuring device 660 and the pressure measuring device 670, if present. As has been described, the interface 330 is enabled for communication with the computing device 805, such that data from the apparatus 804 may be provided to the computing device 805. In some embodiments, the interface 330 further comprises a computing device 710 for processing the signals from the various apparatus within the box 210, with which the interface 330 is in communication. However, in general, control of the apparatus 804 is generally effected via the DQE determination software 740 stored at the computing device 805. Further, the DQE determination software 740 is enabled to receive data from the apparatus 804, images from the image generation device 803 and in turn calculate DQE for the x-ray imaging system. In a non-limiting embodiment, however, the DQE determination software 740 may be stored at the computing device 710, at the apparatus 804, or in the imaging generation device 803, and the computing device 805 is not needed.

Figure 8:
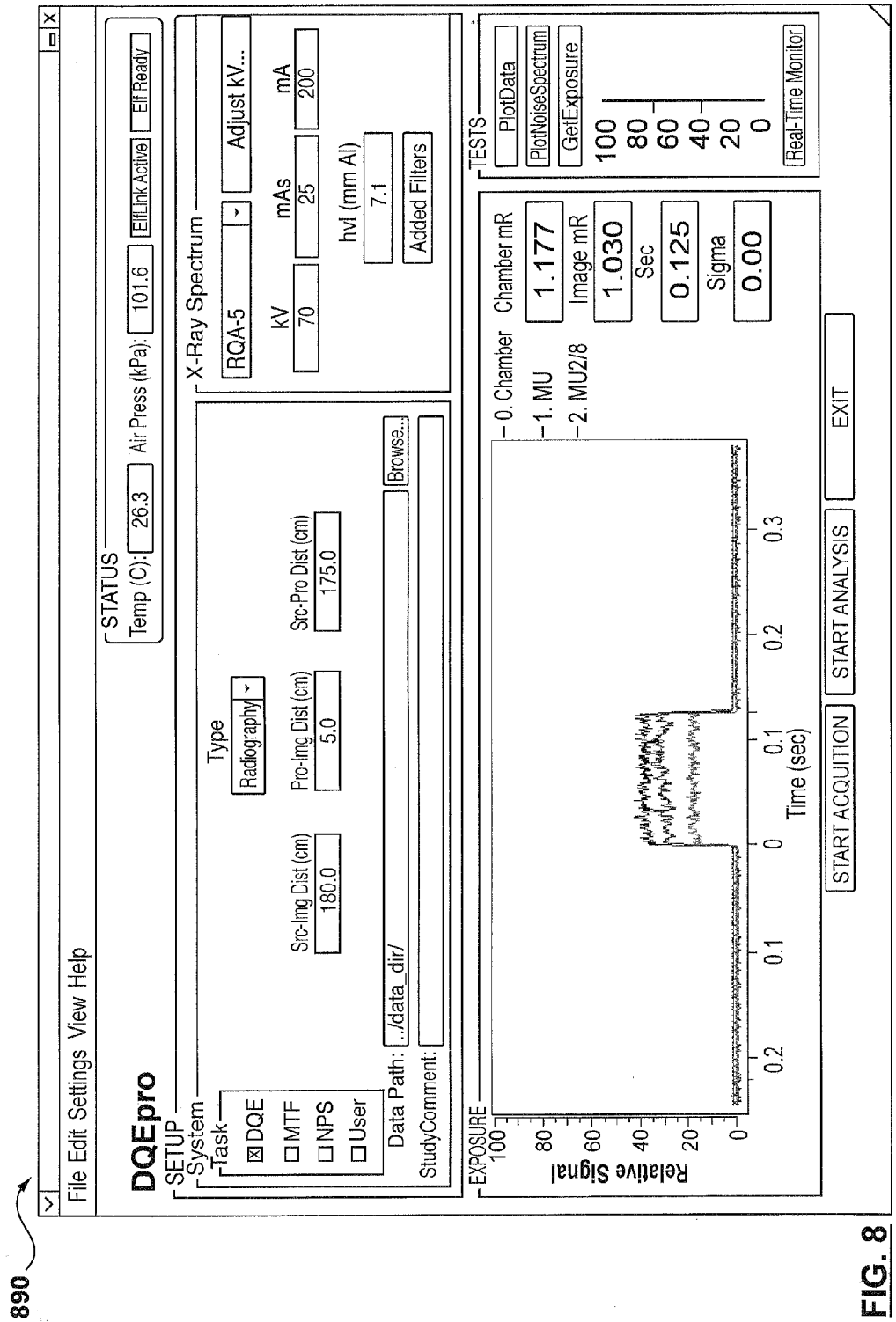
FIG. 8 depicts a graphical user interface controlling an apparatus for assisting determination of detective quantum efficiency (DQE) of an x-ray imaging system, according to a non-limiting embodiment.

A non-limiting embodiment of a graphic user interface (GUI) 890 of the DQE determination software 740 is depicted in FIG. 8. Within the GUI 890, a user may set the distance between the source 802 and the detector 801 ("Src-Img Dist"), and the distance from the detector 801 to a calibrated mark on the box 210 ("Pro-Img Dist"). The DQE determination software 740 is configured to calculate the distance between each module of the apparatus 804, when each module is in use, and the detector 801. Within the GUI 890, the user may also choose a standard x-ray spectrum (as described in IEC62220) that is to be used to make measurements via a pull-down menu (""RQA-5"), or alternatively enter and/or adjust the energy of the x-ray source 802 ("kV"). If a standard spectrum, such as RQA-5, is used, the DQE determination software 740 is further enabled to assist the user in adjusting the hardness of the x-ray beam by prompting the user to insert an appropriate half-value-layer thickness of aluminum in front of the source 802 ("hvl"). This will be described in further detail below.

Figure 9:
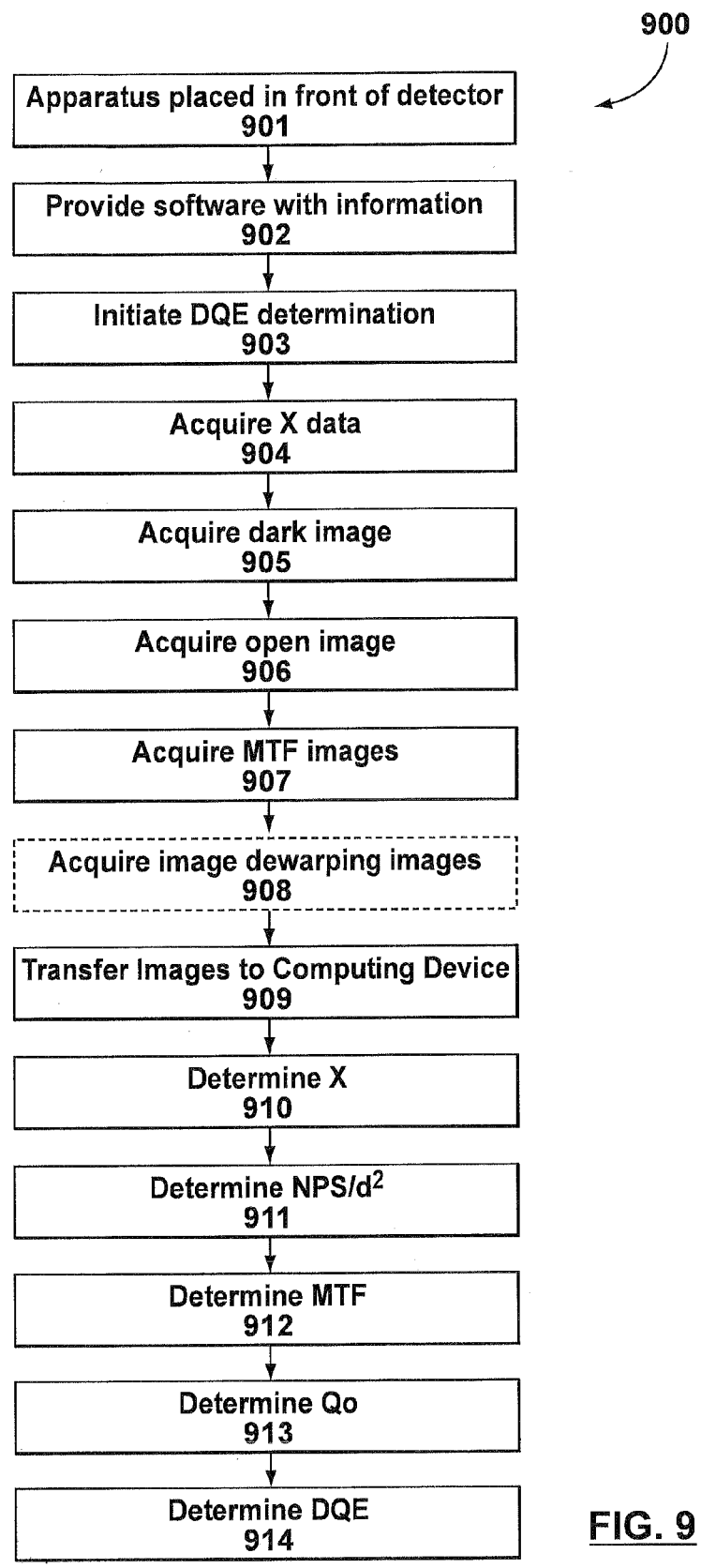
FIG. 9 depicts a method for determination of detective quantum efficiency (DQE) of an x-ray imaging system, according to a non-limiting embodiment.

A method 900 of determining DQE for an imaging system, as in FIG. 1, will now be described with reference to FIG. 9, the apparatus 804 being used for assisting determination of DQE. Furthermore, the following discussion will lead to a further understanding of the apparatus 804. However, it is to be understood that the method 900 and the apparatus 804 can be varied, and need not work exactly as discussed herein in conjunction with each other, and that such variations are within the scope of present embodiments.

It will be recalled from Equation 1 that DQE may be determined if MTF, X, Qo, and $(NPS/d^2)$ are known. Hence, the DQE software 740 is generally enabled to acquire signals from the apparatus 804 and images from the imaging generation device 803 that enable the DQE software 740 to determine MTF, X and $(NPS/d^2)$. Qo may be determined either from tabulated properties of a standard x-ray spectrum, or calculated based on knowledge of a non-standard x-ray spectrum and a measurement of the half-value layer thickness. Hence the method 900 is generally directed towards determining each of the four terms, so that DQE may be determined.

At step 901, the apparatus 804 is placed in the x-ray beam, in front of the input surface of the imaging detector or system being tested, for example detector 801 in FIG. 1. In some embodiments, it may be desirable to place the apparatus 804 as close as possible to the input surface. In other embodiments, it may be desirable to place the apparatus 804 elsewhere, for example between the x-ray source and the input surface of the imaging detector, such as at a patient location. The x-ray beam may be adjusted at the source 802 to expose the window 220a using normal collimation capabilities of the x-ray system, for example as in FIG. 4. The apparatus 804 is connected to the computing device 805 for data input, control and data transfer.

Figure 10:
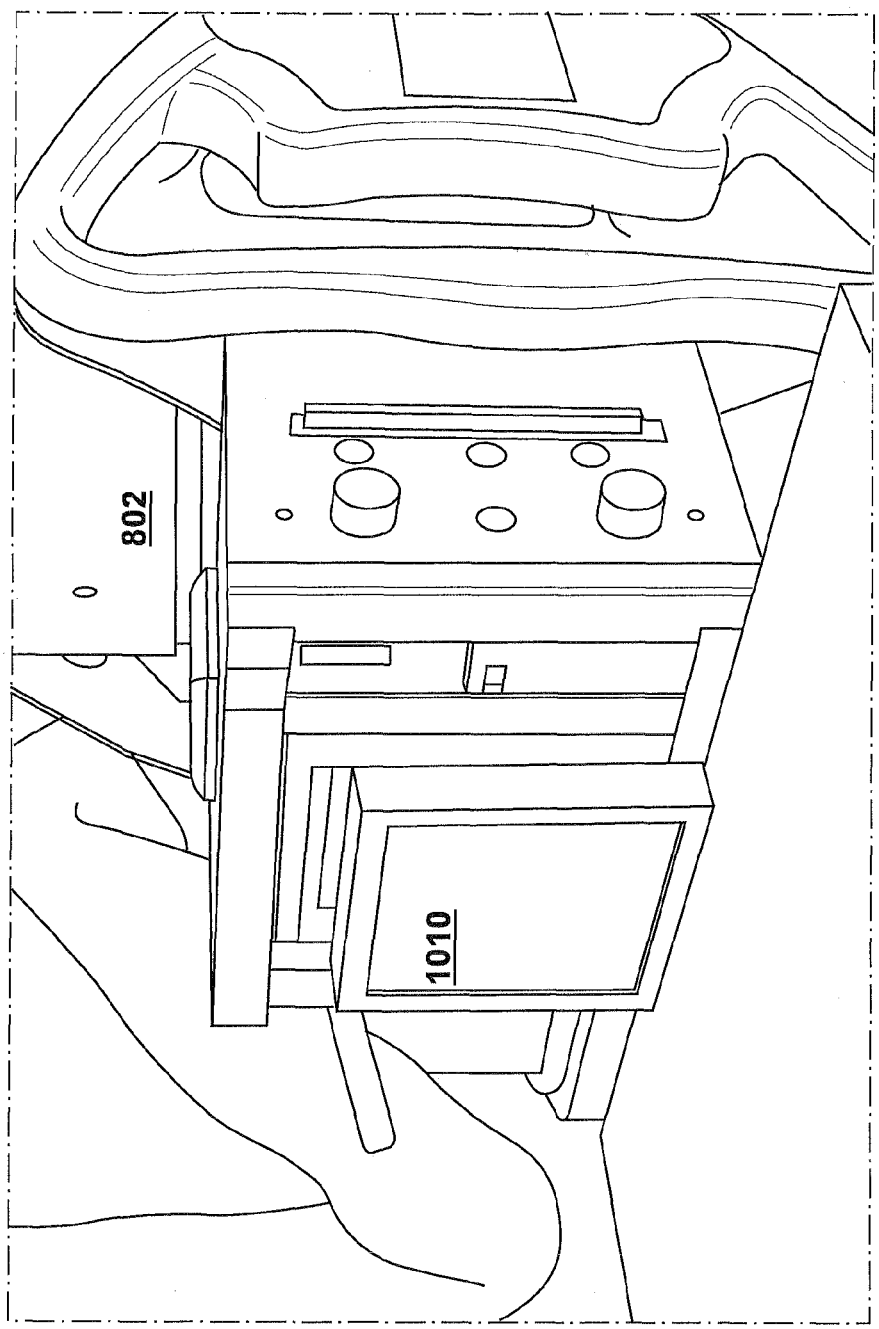
FIG. 10 depicts an x-ray attenuator placed in an x-ray beam to achieve a desired beam hardness, according to a non-limiting embodiment.

In some embodiments, as depicted in FIG. 10, additional x-ray attenuators 1010 may be placed in the x-ray beam as close as possible to the x-ray source 802 to produce an x-ray beam with a desired beam hardness, characterized by the beam's half-value layer thickness. Standards have been proposed for representative spectra in IEC62220. A further description of this process is provided below.

At step 902, information is entered into DQE determination software 740, via the GUI 890, and an input device associated with the computing device 805. This information may include the distance between the source 802 and the detector 801, the distance from the detector 801 and the apparatus 804 (e.g. a calibrated mark on the box 210, as described above), and x-ray spectrum description (mAs, mA, standard spectrum designation or kV and additional filtration materials and thickness of such).

At step 903 DQE determination is initiated by sending various control signals to the apparatus 804.

At step 904 data for determining X is measured by causing the at least one backscatter baffle 610 (or alternatively at least one MTF module 501 and/or 502) and the KERMA module (i.e. module 503) into the space between the aligned windows 220, as in FIG. 6, hence exposing the ionization chamber 507 to the x-ray beam. This may be accomplished by sending a control signal to the interface 330 which in turn controls various motors (e.g. the motor 327) to move the appropriate modules and/or baffles into position. A signal is then received from the ionization chamber 507, via the interface 330 indicative of X (incident free-air exposure or incident free-air KERMA). The ionization chamber 507 is exposed to the x-ray beam to obtain a calibration exposure, embodied in a measured charge (or differential voltage) by the electrometer, as discussed above. With the at least one backscatter baffle 610 in place, along with the at least one scatter baffles 620, x-ray scatter within apparatus 804 is generally eliminated and thus all (or almost all) x-rays that are incident on the ionizing chamber 507 come directly from the x-ray beam. Thus, the measurement is not influenced by the surrounding environment, including different detector designs, geometries, and configurations.

The temperature and/or pressure inside the box at the time of measurement may also be acquired at step 905, via the interface 330, if the temperature measuring device 660 and/or the pressure measuring device 670 are present.

Further, calibration data for calibrating the at least one monitor x-ray detector 650 may be acquired during step 905, in which the signal from the at least one monitor x-ray detector 650 is acquired during the calibration exposure. Hence, using the signals that are acquired from the ionization chamber 507 and the at least one monitor x-ray detector 650 a calibration factor may be determined for the at least one x-ray detector 650, which may be used to determine fluctuations of X which occur during later image acquisitions.

At step 905, a "dark image" is acquired, a dark image being the response of the detector 801 when no clear path for x-rays exists through the apparatus 804 (i.e. x-rays being absorbed), and is used in the determination of DQE, as described below. This may be achieved by prompting a user to perform an x-ray exposure and acquire an image after placing an x-ray absorbing material in the path of the x rays to block passage of the x rays to detector 801. Alternatively, a separate dark image acquisition step may be performed in which a control signal is transmitted to the apparatus 804 to cause the at least one backscatter module 610 (or at least one MTF module 501 and/or 502) to move into the space between the aligned windows 220 prior to an image being acquired.

At step 906, at least one "open image" is acquired, an open image being the response of the detector 801 when a clear path for x-rays exists through the apparatus 804 (i.e. no x-rays being absorbed), and is used in the determination of DQE, as described below. This may be achieved by sending a control signal to the interface 330 instructing the apparatus 804 to remove all modules from the space between the aligned windows 220 (i.e. the x-ray path). While in some embodiments a single open image may suffice, it is generally desirable to acquire a plurality of open images, for example approximately 24 images. The signal from the at least one monitor x-ray detector 650, if present, is also acquired during each image acquisition.

At step 907 MTF images/edge images are acquired by sending a signal to the interface 330 which causes at least one MTF module (e.g. module 501 and/or module 502) to move into the space between the aligned windows 220 (i.e. the x-ray path). The user is then prompted to acquire an image. Step 907 is repeated with additional edge modules as desired. The signal from the at least one monitor x-ray detector 650, if present, is also acquired during each image acquisition. In an alternative embodiment, edge images can be acquired while the at least one MTF module is moving through the space between the aligned windows 220, in order to obtain a measure of temporal MTF and/or spatial temporal MTF, or other types of MTF that are motion and/or time dependent. This measure of MTF that are motion and/or time dependent may be useful in applications such as fluoroscopy, and to determine the DQE of fluoroscopic imaging systems.

At an optional step 908, image dewarping images are acquired by sending a signal to the interface 330 which causes the module 504 (i.e. the BB module) to move into the space between the aligned windows 220 (i.e. the x-ray path). The user is then prompted to acquire an image. The same measurement may also be used in pixel-size determination.

As each of the KERMA module, the at least one backscatter baffle and the at least one MTF module are independently moveable in and out the x-ray beam passing through the box 210, at least one open image, a dark image, and at least one edge image (i.e. MTF image) may be independently acquired by the x-ray imaging system, and KERMA module measurements may be performed independent of image acquisition, such that the images and the KERMA module measurements may be processed to determine DQE, as will now be described.

At step 909, the acquired images are transferred to the computing device 805, if necessary (i.e. if the computing device 805 has not yet received the acquired images from the image generation device 803, the acquired images are transferred via CDROM, DVD, network interface, and the like). Exposure data from each acquired image may also be transferred and coordinated with each acquired image. The imaging generation device 803 may correct acquired images for dark-current offsets, bad pixels, or pixel gain corrections, but otherwise it is desirable that acquired images be unprocessed or "raw" images. If images have been processed using a non-linear algorithm, it may be desirable to linearize images to ensure that average pixel value (d) is proportional to the air exposure or KERMA incident on the detector prior to determination of the DQE.

At step 910, X at the detector 801 is calculated, and specifically at the image plane of the detector 801 (i.e. the plane in which an image is generally acquired at the detector). As X at the ionization chamber 507 may be determined from the measured charge acquired at step 905 incident air-KERMA value (and/or incident free air exposure) corresponding to the position of the image plane of the detector 801 may be calculated using the inverse-square law, as the distance from the ionization chamber 507 to the detector 801 is known, as known to one of skill in the art. In addition the X at the detector 801 may be corrected for air temperature and pressure, and energy response using half-value layer (HVL) of the x-ray beam.

At step 911, the NPS/d2 is determined using the open images acquired at step 906. In one non-limiting embodiment NPS/d2 may be calculated using the following calculation and formula as known to one of skill in the art.

The normalized NPS describing the spectral decomposition of image noise as a function of spatial frequency u in the x direction is given by $$NPS_x(u)/d^2 = \frac{a_x a_y}{d^2 N_x N_y} \left\langle \left| DFT\left\{ \sum_{j=0}^{N_y-1} d_{i,j} - d \right\} \right|^2 \right\rangle \quad \text{(Equation 3)}$$

where d is the average dark-subtracted pixel value in the open images used to determine the NPS (i.e. average pixel value of each open image minus the dark pixel value determined from dark image acquired at step 905), $a_x$ and $a_y$ are the x and y pixel dimensions, and $N_x$ and $N_y$ are the number of pixels in each sub-image, in the x and y directions respectively, used to determine the NPS (in general, each open image is divided into a number of sub-images, for example 16 sub-images, for this calculation), Further, this calculation makes use of a discrete Fourier transform DFT{ }, and $d_{i,j}$ is the dark-subtracted pixel value in the i-th column and j-th row of the sub image, as known to one of skill in the art. The NPS calculated with this equation includes any noise aliasing present in image data. However other methods of calculating $NPS/d^2$ are within the scope of present embodiments. Further, each image may be corrected based on the calibration factor and the signal from the at least one x-ray detector 650 acquired during image acquisition. A similar equation exists for the NPS in the y direction.

At step 912, MTF is calculated using the edge images acquired at step 907. In one non-limiting embodiment, MTF is calculated using the "slanted-edge" method as known to one of skill in the art. In this method, at least one open image acquired at step 906, the dark image acquired at step 905 and the edge images acquired at step 907 are processed. Temporal MTF may also be calculated at step 912 in embodiments where images of the MTF module moving through space between the aligned windows 220 were acquired.

At step 913, Qo may be determined if necessary, for example by obtaining Qo from a table of standardized spectra, such as Table 1.

TABLE 1

Properties of Standardized Spectra

| Spectrum | Nominal kV | HVL (mmAL) | Additional Filtration (mmAl) | Qo (mm$^{-2}$nGy$^{-1}$) | Qo (mm$^{-2}$R$^{-1}$) |
|---|---|---|---|---|---|
| RQA 3 | 50 | 4.0 | 10.0 | 21.759 | 1.89 × 10$^8$ |
| RQA 5 | 70 | 7.1 | 21.0 | 30.174 | 2.62 × 10$^8$ |
| RQA 7 | 90 | 9.1 | 30.0 | 32.362 | 2.81 × 10$^8$ |
| RQA 9 | 120 | 11.5 | 40.0 | 31.077 | 2.70 × 10$^8$ |

Alternatively, Qo may be determined based on knowledge of a non-standard x-ray spectrum and a measurement of the half-value layer thickness, as known to one of skill in the art.

At step 914, the values of X, NPS/d$^2$, MTF and Qo, determined at steps 910, 911, 912 and 913 are used to determine DQE using Equation 1.

While method 900 has been described with reference to steps 902 through 914 being in the depicted order, it is understood that the order of steps 902 through 914 may be varied. For example, the image acquisition steps may occur prior to the acquisition of data from the ionization chamber 507. Further, determination steps may occur in parallel with image and data acquisition steps.

In some embodiments, the geometric accuracy of the imaging system may also determined. This is accomplished by moving the BB module (module 504) into the x-ray beam and acquiring a geometric correction (or "BB") image. Using the combination of this image with an open and a dark image, the centre-to-centre spacing of each pixel in the x and y directions in the image plane may be determined. The process may be automated so that detection of the BBs in the image and calculation of the pixel dimensions is automatic and does not require operator intervention. Some imaging systems introduce geometric distortions in the image in which pixel dimensions and positions vary across the image in an undesirable manner. For these systems, the BB image is used to determine correction coefficients that allow "de-warping" algorithms known to persons of skill in the art to be used to correct for image geometric distortions. The DQE determination software 740 may comprise such de-warping algorithms.

In some embodiments, the DQE determination software 740 may be enabled to implement a semi-automated method to adjust the kV of the generator in the x-ray source 802 to ensure the beam half-value layer (HVL) thickness is equal to the desired tabulated value for standard spectra. The DQE determination software 740 prompts the user to place a standard thickness of aluminum in the x-ray beam close to the x-ray source 802 and to acquire an exposure. The apparatus 804 is then triggered to measure the free-air exposure, as described above with reference to step 904, for calibration exposures. The DQE determination software 740 then prompts the user to place additional aluminum in the x-ray beam with a thickness equal to the desired HVL thickness and acquire another exposure. The apparatus 804 is then triggered to measure the free-air exposure for the second exposure. The DQE determination software 740 then estimates what change in generator kV setting is required to ensure that the second exposure is equal to half of the first, if necessary. When no additional change in kV setting is required, the beam HVL is equal to the desired HVL.

Figure 11D:
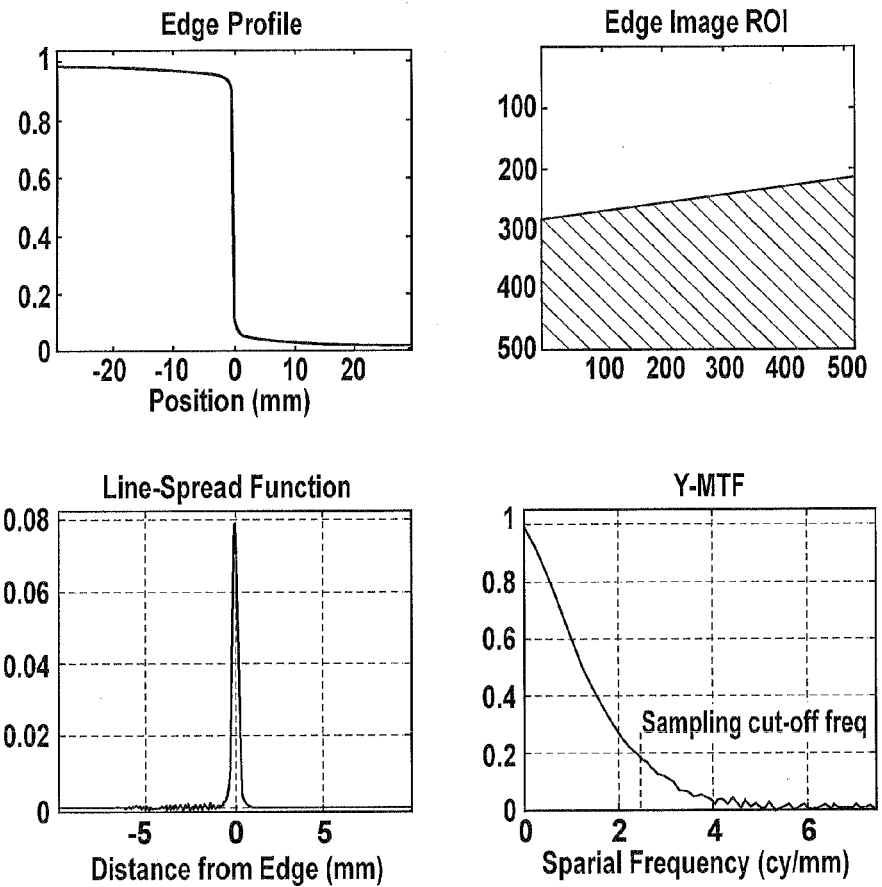
Figure 11E:
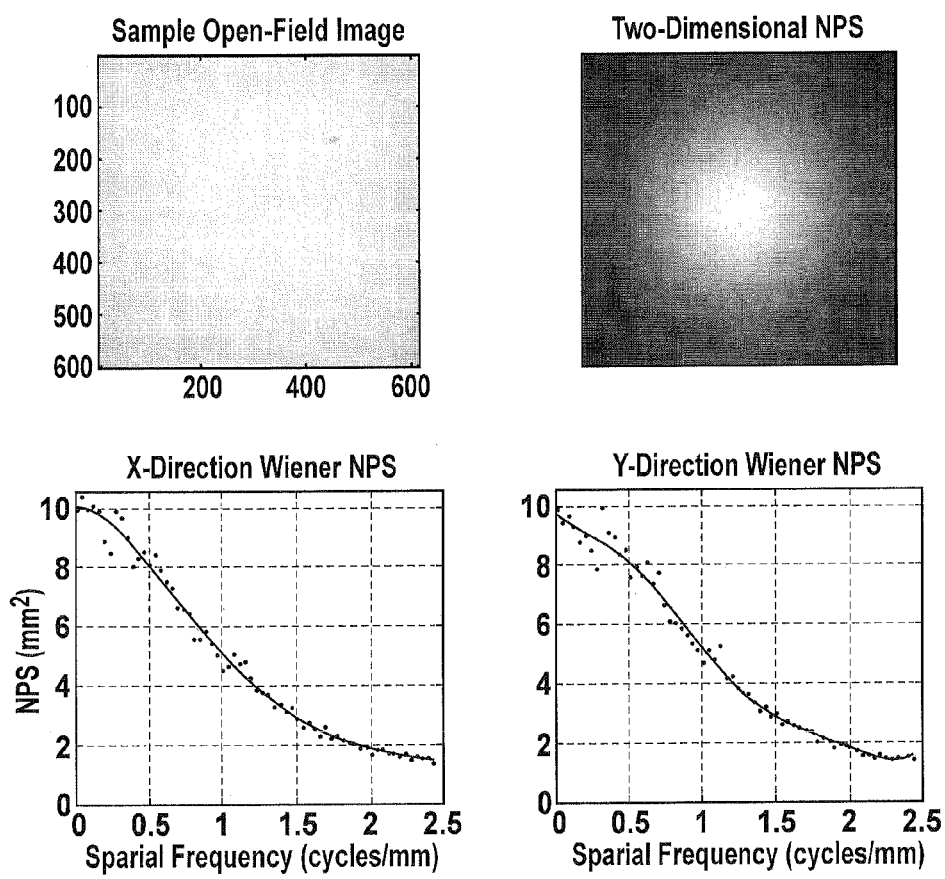
Figure 11F:
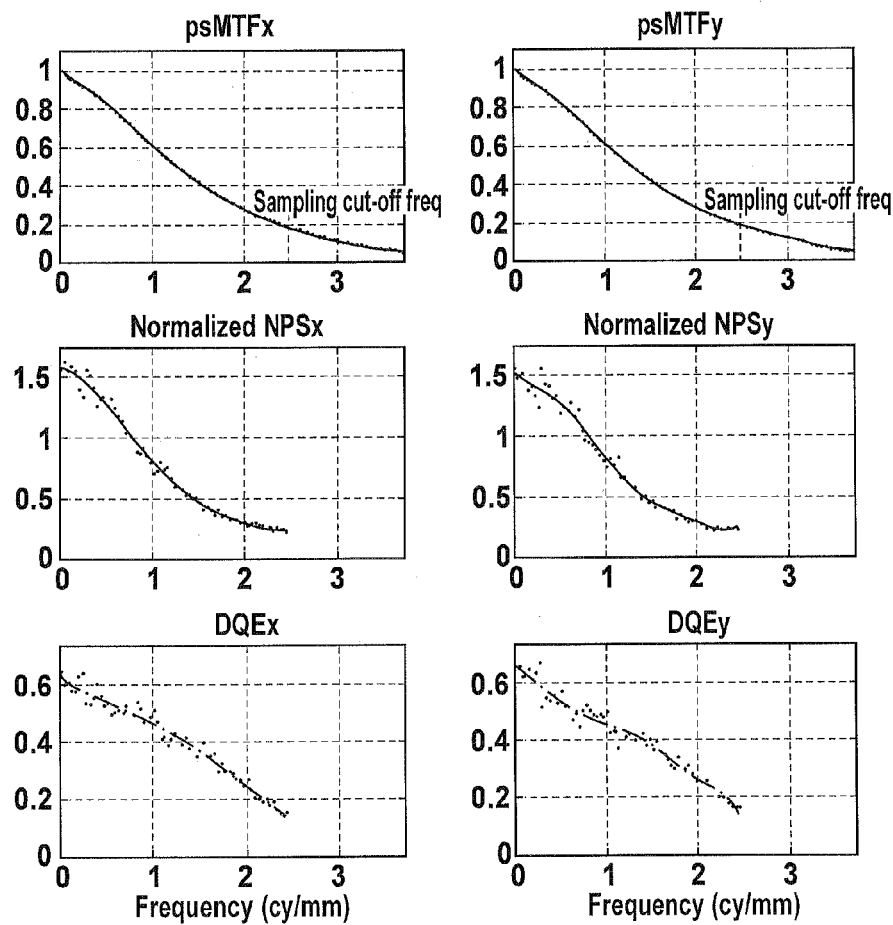

A successful prototype of the apparatus 804 and the DQE determination software 740 was built. Testing of x-ray imaging system was performed using the prototype and DQE was determined for the imaging system. DQE determined via the prototype was within 5% of the published DQE for a similar imaging system. The prototype of the DQE determination software 740 was further configured to provide a report of measurements. A non-limiting embodiment of the report is depicted in FIGS. 11a through 11f. FIG. 11a depicts an acquired dark image and acquired open images. FIG. 11b depicts an acquired open image, an acquired BB image, and acquired edge images. FIGS. 11c and 11d depict a report on determination of MTF. FIG. 11e depicts a report on determination of NPS. FIG. 11f depicts a report on determination of DQE.

While embodiments have been described with reference to an x-ray detector in an x-ray imaging system, it is understood that the apparatus 804 may be used for assisting determination of DQE of any type of ionizing radiation imaging system employing a detector of any type of suitable ionizing radiation. For example, the apparatus 804 may be used in nuclear medicine imaging systems using gamma radiation from radioisotopes. Further, apparatus 804 may be used for assisting determination of DQE detectors used in computed-tomography systems, fluoroscopy systems, mammography systems, dental systems, veterinary systems, and the like, including digital detectors, flat-panel detectors, computed radiography (CR) detectors, film detectors, phosphor-based detectors, semi-conductor-based detectors, image-intensifier-based systems. Other types of detectors will occur to one of skill in the art.

Finally, while the apparatus 804 has been described with reference to assisting determination of DQE of an ionizing radiation imaging system, in some embodiments it may be desirable to use the apparatus 804 to assist determination of MTF of an ionizing radiation imaging system, without necessarily determining DQE. Hence the apparatus 804 may be employed for assisting determination of at least one of modulation transfer function (MTF) and detective quantum efficiency (DQE) of an ionizing radiation imaging system.

Those skilled in the art will appreciate that in some embodiments, the functionality of the DQE determination software 740 may be implemented using pre-programmed hardware or firmware elements (e.g., application specific integrated circuits (ASICs), electrically erasable programmable read-only memories (EEPROMs), etc.), or other related components. In other embodiments, the functionality of the DQE determination software 740 may be achieved using a computing apparatus that has access to a code memory (not shown) which stores computer-readable program code for operation of the computing apparatus. The computer-readable program code could be stored on a medium which is fixed, tangible and readable directly by these components, (e.g., removable diskette, CD-ROM, ROM, fixed disk, USB drive), or the computer-readable program code could be stored remotely but transmittable to these components via a modem or other interface device connected to a network (including, without limitation, the Internet) over a transmission medium. The transmission medium may be either a non-wireless medium (e.g., optical or analog communications lines) or a wireless medium (e.g., microwave, infrared, free-space optical or other transmission schemes) or a combination thereof.

Persons skilled in the art will appreciate that there are yet more alternative implementations and modifications possible for implementing the embodiments, and that the above implementations and examples are only illustrations of one or more embodiments. The scope, therefore, is only to be limited by the claims appended hereto.

What is claimed is:

1. An apparatus for assisting determination of at least one of modulation transfer function (MTF) and detective quantum efficiency (DQE) of an ionizing radiation imaging system, the ionizing radiation imaging system including an ionizing radiation detector for detecting an ionizing radiation beam received from an ionizing radiation source, the apparatus comprising,
- a box comprising a front window and rear window, the front window and the rear window being generally aligned and defining a space there between within the box, each of the front window and the rear window being generally transparent to ionizing radiation and of an area substantially similar to the ionizing radiation beam such that, when said box is placed in front of the detector, the ionizing radiation beam may substantially pass through said front window and said rear window, and into said detector;
- a KERMA (kinetic energy released in medium) module, contained within said box between said front window and said rear window, for measuring at least one of incident free-air exposure and incident free-air KERMA of the ionizing radiation beam when the ionizing radiation beam passes through said space, said KERMA module comprising a scatter baffle and an ionization chamber residing substantially in an aperture through said scatter baffle, said aperture being smaller than the front window, said scatter baffle comprising a sheet of ionizing radiation absorbing material for further preventing scatter of the ionizing radiation within said box;
- at least one backscatter baffle located between said KERMA module and said rear window for preventing backscatter of the ionizing radiation beam from the detector into the KERMA module, when said KERMA module is in use;
- at least one MTF module, contained within said box, for enabling acquisition of at least one edge image by the ionizing radiation imaging system,
- each said KERMA module, said at least one backscatter baffle and said at least one MTF module being independently moveable in and out of said space, such that at least one open image, a dark image, and said at least one edge image may be independently acquired by the ionizing radiation imaging system when the ionizing radiation beam passes through said box, and KERMA module measurements may be performed independent of image acquisition, such that said images and said KERMA module measurements may be processed to determine DQE;
- an interface for acquiring data from said KERMA module, and for controlling moving of each said KERMA module, said at least one backscatter baffle, and said at least one MTF module in and out of said space; and
- a self-contained unit comprising said box, said KERMA module, said at least one backscatter baffle, and said at least one MTF module.

2. The apparatus of claim 1, further comprising at least one monitor ionizing radiation detector within said box, enabled to engage the ionizing radiation beam and produce a signal proportional to at least one of the incident ionizing radiation exposure and KERMA, said interface enabled for acquiring data from said at least one monitor ionizing radiation detector.

3. The apparatus of claim 1, wherein each of said front window and said rear window comprises a sheet of an ionizing radiation transparent material covering a said aperture in said box.

4. The apparatus of claim 1, further comprising: a front scatter baffle adjacent said front window, the front scatter baffle for preventing scatter of the ionizing radiation beam within said box into the KERMA module, and to reduce backscatter that may be generated from said backscatter baffle, when said KERMA module is in use; and, a rear scatter baffle adjacent said rear window.

5. The apparatus of claim 1 further comprising at least one of an electrometer and current amplifier in communication with said ionization chamber.

6. The apparatus of claim 1, wherein said at least one backscatter baffle is enabled to reside between said KERMA module and a detector facing side of said box, when said KERMA module is in use, such that ionizing radiation passing through said KERMA module is generally absorbed by said backscatter baffle.

7. The apparatus of claim 6, wherein said at least one backscatter baffle comprises said at least one MTF module.

8. The apparatus of claim 1, further comprising a temperature measuring device in communication with said interface for measuring the temperature inside said box, such that measurements of DQE may be temperature corrected.

9. The apparatus of claim 1, further comprising a pressure measuring device in communication with said interface for measuring the pressure inside said box, such that measurements of DQE may be pressure corrected.

10. The apparatus of claim 1, further comprising at least one motion control unit for moving each said KERMA module, said at least one backscatter baffle, and said at least one MTF module in and out of said space.

11. The apparatus of claim 10, wherein said at least one motion control unit comprises at least one of a slideable apparatus, a pivotable apparatus, and a rotatable apparatus.

12. The apparatus of 10, wherein said at least one motion control unit comprises a motor in communication with said interface, said motor for moving of each said KERMA module, said at least one backscatter baffle, and said at least one MTF module in and out of said space.

13. The apparatus of claim 10, wherein said interface comprises a manual interface for manually controlling said at least one motion control unit.

14. The apparatus of claim 1, further comprising a geometric correction module for enabling acquisition of at least one geometric correction image by the ionizing radiation imaging system, said at least one geometric correction image for determining geometric correction coefficients that enable a de-warping algorithm used in the correction of image geometric distortions, said geometric correction module being independently moveable in and out of said space such that said geometric correction image may be acquired independent of said at least one open image, said dark image, said at least one edge image and said KERMA module measurements.

15. The apparatus of claim 1, wherein said at least one MTF module comprises an area that generally absorbs ionizing radiation and an area that is generally transparent to ionizing radiation, wherein the intersection of each said area defines at least one of an edge in an x-direction and an edge in a y-direction.

16. The apparatus of claim 1, wherein said at least one MTF module is enabled to move through said space during said acquisition of said at least one edge image to enable measurement of an MTF that is at least one of motion dependent and time dependent.

17. The apparatus of claim 1, wherein said ionizing radiation comprises at least one of x-rays and gamma radiation.

18. The apparatus of claim 1, wherein the ionizing radiation imaging system comprises at least one of a computed-tomography system, a fluoroscopy system, a mammography imaging system, a dental imaging system, a veterinary imaging system, and a nuclear medicine imaging system.

19. The apparatus of claim 1, wherein the ionizing radiation detector comprises at least one of a digital detector, a flat-panel detector, a computed radiography (CR) detector, a film detector, a phosphor-based detector, a semi-conductor-based detector, an image-intensifier-based detector, an x-ray detector and a gamma radiation detector.

20. A system for determining at least one of modulation transfer function (MTF) and detective quantum efficiency (DQE) of an ionizing radiation imaging system comprising,
   an apparatus for assisting determination of at least one of said MTF and said DQE of an ionizing radiation imaging system, the ionizing radiation imaging system including an ionizing radiation detector for detecting an ionizing radiation beam received from an ionizing radiation source, the apparatus comprising,
      a box comprising a front window and rear window, the front window and the rear window being generally aligned and defining a space there between within the box, each of the front window and the rear window being generally transparent to ionizing radiation and of an area substantially similar to the ionizing radiation beam such that, when said box is placed in front of the detector, the ionizing radiation beam may substantially pass through said front window and said rear window, and into said detector;
      a KERMA (kinetic energy released in medium) module, contained within said box between said front window and said rear window, for measuring at least one of incident free-air exposure and incident free-air KERMA of the ionizing radiation beam when the ionizing radiation beam passes through said space, said KERMA module comprising a scatter baffle and an ionization chamber residing substantially in an aperture through said scatter baffle, said aperture being smaller than the front window, said scatter baffle comprising a sheet of ionizing radiation absorbing material for further preventing scatter of the ionizing radiation within said box;
      at least one backscatter baffle located between said KERMA module and said rear window for preventing backscatter of the ionizing radiation beam from the detector into the KERMA module, when said KERMA module is in use;
      at least one MTF module, contained within said box, for enabling acquisition of at least one edge image by the ionizing radiation imaging system,
      each said KERMA module, said at least one backscatter baffle and said at least one MTF module being independently moveable in and out of said space, such that at least one open image, a dark image, and said at least one edge image may be independently acquired by the ionizing radiation imaging system when the ionizing radiation beam passes through said box, and KERMA module measurements may be performed independent of image acquisition, such that said images and said KERMA module measurements may be processed to determine DQE;
      an interface for acquiring data from said KERMA module, and for controlling moving of each said KERMA module, said at least one backscatter baffle, and said at least one MTF module in and out of said space; and,
      a self-contained unit comprising said box, said KERMA module, said at least one backscatter baffle, and said at least one MTF module, and
   a computing device enabled to receive said at least one open image, said dark image, said at least one edge image, and said KERMA module measurements, said computing device comprising,
      a memory for storing said at least one open image, said dark image, said at least one edge image, said KERMA module measurements and DQE determination software enabled for:
         determining at least one of incident free-air exposure and incident free-air KERMA of the ionizing radiation beam at an image plane of the detector, based on said KERMA module measurements and distance between said KERMA module and said image plane;
         determining the MTF of the imaging system by processing said at least one open image, said dark image, said at least one edge image;
         determining a noise power spectrum (NPS) of the imaging system by processing said at least one open image and said dark image;
         determining an average pixel value of said at least one open image by processing said at least one open image and said dark image;
         determining the number of ionizing radiation photons per unit area and exposure (Qo);
         and determining DQE of the image system by processing said at least one of incident free-air exposure and incident free-air KERMA of the ionizing radiation beam at the image plane of the detector, said MTF, said NPS, said average pixel value and said Qo; and
      a processor for processing said DQE determination software.

* * * * *